(12) United States Patent
Mirkin et al.

(10) Patent No.: US 7,147,687 B2
(45) Date of Patent: *Dec. 12, 2006

(54) NON-ALLOYING CORE SHELL NANOPARTICLES

(75) Inventors: Chad A. Mirkin, Wilmette, IL (US);
Yun-Wei Cao, Evanston, IL (US);
Rongchao Jin, Evanston, IL (US)

(73) Assignee: Nanosphere, Inc., Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/153,483

(22) Filed: May 22, 2002

(65) Prior Publication Data

US 2003/0129608 A1    Jul. 10, 2003

Related U.S. Application Data

(63) Continuation-in-part of application No. 10/034,451, filed on Dec. 28, 2001, and a continuation-in-part of application No. PCT/US01/50825, filed on Dec. 28, 2001.

(60) Provisional application No. 60/293,861, filed on May 25, 2001.

(51) Int. Cl.
B22F 1/00 (2006.01)
B22F 9/00 (2006.01)
C21B 15/04 (2006.01)
C22B 5/20 (2006.01)
B82B 3/00 (2006.01)

(52) U.S. Cl. .......................... 75/343; 75/362; 997/702; 997/704; 997/712; 997/810

(58) Field of Classification Search .................. 435/6; 536/23.1, 24.3
See application file for complete search history.

(56) References Cited

U.S. PATENT DOCUMENTS

| | | | |
|---|---|---|---|
| 4,193,983 A | 3/1980 | Ullman et al. | |
| 4,256,834 A | 3/1981 | Zuk et al. | |
| 4,261,968 A | 4/1981 | Ullman et al. | |
| 4,313,734 A | 2/1982 | Leuvering | |
| 4,318,707 A | 3/1982 | Litman et al. | |
| 4,650,770 A | 3/1987 | Liu et al. | |
| 4,713,348 A | 12/1987 | Ullman | |
| 4,853,335 A | 8/1989 | Olsen et al. | |
| 4,868,104 A | 9/1989 | Kurn et al. | |
| 4,996,143 A | 2/1991 | Heller et al. ................... 435/6 |
| 5,225,064 A | 7/1993 | Henkens et al. | |
| 5,284,748 A | 2/1994 | Mroczkowski et al. | |
| 5,288,609 A | 2/1994 | Engelhardt et al. | |
| 5,294,369 A | 3/1994 | Shigekawa et al. | |
| 5,360,895 A | 11/1994 | Hainfeld et al. | |
| 5,384,073 A | 1/1995 | Shigekawa et al. | |
| 5,384,265 A | 1/1995 | Kidwell et al. | |
| 5,460,831 A | 10/1995 | Kossovsky et al. | |
| 5,472,881 A | 12/1995 | Beebe et al. | |
| 5,508,164 A | 4/1996 | Kausch et al. ................... 435/6 |
| 5,514,602 A | 5/1996 | Brooks, Jr. et al. | |
| 5,521,289 A | 5/1996 | Hainfeld et al. | |
| 5,543,158 A | 8/1996 | Gref et al. | |
| 5,571,726 A | 11/1996 | Brooks, Jr. et al. | |
| 5,599,668 A | 2/1997 | Stimpson et al. | |
| 5,609,907 A | 3/1997 | Natan | |
| 5,637,508 A | 6/1997 | Kidwell et al. | |
| 5,665,582 A | 9/1997 | Kausch et al. | |
| 5,681,943 A | 10/1997 | Letsinger et al. | |
| 5,751,018 A | 5/1998 | Alivisatos et al. | |
| 5,830,986 A | 11/1998 | Merrill et al. ............... 528/332 |
| 5,900,481 A | 5/1999 | Lough et al. ............... 536/55.3 |
| 5,922,537 A | 7/1999 | Ewart et al. .................... 435/6 |
| 5,939,021 A | 8/1999 | Hansen et al. | |
| 5,972,615 A | 10/1999 | An et al. ......................... 435/6 |
| 5,990,479 A | 11/1999 | Weiss et al. | |
| 6,025,202 A | 2/2000 | Natan | |
| 6,149,868 A | 11/2000 | Natan et al. | |
| 6,159,378 A | 12/2000 | Holman et al. ............. 210/695 |
| 6,180,415 B1 | 1/2001 | Schultz et al. .............. 436/518 |
| 6,203,989 B1 | 3/2001 | Goldberg et al. .............. 435/6 |
| 6,214,560 B1 | 4/2001 | Yguerabide et al. | |
| 6,251,303 B1 | 6/2001 | Bawendi et al. ...... 252/301.4 R |
| 6,264,825 B1 | 7/2001 | Blackburn et al. ........ 205/777.5 |
| 6,277,489 B1 | 8/2001 | Abbott et al. ............... 428/403 |
| 6,306,610 B1 | 10/2001 | Bawendi et al. ............. 435/7.1 |
| 6,344,272 B1 | 2/2002 | Oldenburg et al. ......... 428/403 |
| 6,361,944 B1 | 3/2002 | Mirkin et al. .................... 435/6 |
| 6,365,418 B1 | 4/2002 | Wagner et al. .............. 436/518 |
| 6,417,340 B1 | 7/2002 | Mirkin et al. .............. 536/23.1 |
| 6,428,811 B1 | 8/2002 | West et al. .................. 424/497 |
| 6,495,324 B1 | 12/2002 | Mirkin et al. .................... 435/6 |
| 6,506,564 B1 * | 1/2003 | Mirkin et al. .................... 435/6 |

(Continued)

FOREIGN PATENT DOCUMENTS

EP    0 630 974 A2    6/1994

(Continued)

OTHER PUBLICATIONS

Mathe, Z., ""Electroless" or Autocatalytic Gold Plating", Metal Finishing, vol. 90, pp. 33-39 (1992).*

(Continued)

*Primary Examiner*—Teresa E. Strzelecka
(74) *Attorney, Agent, or Firm*—McDonell Bohhnen, Hulbert & Berghoff LLP

(57) ABSTRACT

The present invention relates composite core/shell nanoparticles and a two-step method for their preparation. The present invention further relates to biomolecule-core/shell nanoparticle conjugates and methods for their preparation. The invention also relates to methods of detection of biomolecules comprising the biomolecule-core/shell nanoparticle conjugates.

14 Claims, 9 Drawing Sheets

U.S. PATENT DOCUMENTS

| | | | |
|---|---|---|---|
| 6,530,944 B1 | 3/2003 | West et al. ............... | 607/88 |
| 6,579,721 B1 | 6/2003 | Natan et al. .............. | 436/164 |
| 6,582,921 B1 | 6/2003 | Mirkin et al. ............. | 435/6 |
| 6,602,669 B1 | 8/2003 | Letsinger et al. .......... | 435/6 |
| 6,610,491 B1 | 8/2003 | Mirkin et al. ............. | 435/6 |
| 6,645,517 B1 | 11/2003 | West et al. ............... | 424/422 |
| 6,645,721 B1 | 11/2003 | Mirkin et al. ............. | 435/6 |
| 6,660,381 B1 | 12/2003 | Halas et al. .............. | 428/403 |
| 6,673,548 B1 | 1/2004 | Mirkin et al. ............. | 435/6 |
| 6,677,122 B1 | 1/2004 | Mirkin et al. ............. | 435/6 |
| 6,682,895 B1 | 1/2004 | Mirkin et al. ............. | 435/6 |
| 6,685,730 B1 | 2/2004 | West et al. ............... | 607/89 |
| 6,685,986 B1 | 2/2004 | Oldenburg et al. ......... | 427/214 |
| 6,699,724 B1 | 3/2004 | West et al. ............... | 436/525 |
| 6,709,825 B1 | 3/2004 | Mirkin et al. ............. | 435/6 |
| 6,720,147 B1 | 4/2004 | Mirkin et al. ............. | 435/6 |
| 6,720,411 B1 | 4/2004 | Mirkin et al. ............. | 536/23.1 |
| 6,726,847 B1 | 4/2004 | Mirkin et al. ............. | 216/90 |
| 6,730,269 B1 | 5/2004 | Mirkin et al. ............. | 422/68.1 |
| 6,740,491 B1 | 5/2004 | Mirkin et al. ............. | 435/6 |
| 6,750,016 B1 | 6/2004 | Mirkin et al. ............. | 435/6 |
| 6,759,199 B1 | 7/2004 | Mirkin et al. ............. | 435/6 |
| 6,767,702 B1 | 7/2004 | Mirkin et al. ............. | 435/6 |
| 6,773,884 B1 | 8/2004 | Mirkin et al. ............. | 435/6 |
| 6,777,186 B1 | 8/2004 | Mirkin et al. ............. | 435/6 |
| 6,778,316 B1 | 8/2004 | Halas et al. .............. | 359/296 |
| 6,783,569 B1* | 8/2004 | Cheon et al. .............. | 75/348 |
| 6,852,252 B1 | 2/2005 | Halas et al. .............. | 252/582 |
| 6,875,475 B1 | 4/2005 | Moran et al. ............. | 427/437 |
| 2002/0068187 A1* | 6/2002 | O'Connor et al. ......... | 428/546 |
| 2002/0137070 A1 | 9/2002 | Mirkin et al. ............. | 435/6 |
| 2002/0155461 A1 | 10/2002 | Mirkin et al. ............. | 435/6 |
| 2002/0160381 A1 | 10/2002 | Mirkin et al. ............. | 435/6 |
| 2002/0177143 A1 | 11/2002 | Mirkin et al. ............. | 435/6 |
| 2002/0192687 A1 | 12/2002 | Mirkin et al. ............. | 435/6 |
| 2003/0054358 A1 | 3/2003 | Mirkin et al. ............. | 435/6 |
| 2003/0068622 A1 | 4/2003 | Mirkin et al. ............. | 435/6 |
| 2003/0068638 A1 | 4/2003 | Mirkin et al. ............. | 435/6 |
| 2003/0087242 A1 | 5/2003 | Mirkin et al. ............. | 435/6 |
| 2003/0113740 A1 | 6/2003 | Mirkin et al. ............. | 435/6 |
| 2003/0124528 A1 | 7/2003 | Mirkin et al. ............. | 435/6 |
| 2003/0129608 A1 | 7/2003 | Mirkin et al. ............. | 435/6 |
| 2003/0143538 A1 | 7/2003 | Mirkin et al. ............. | 435/6 |
| 2003/0143598 A1 | 7/2003 | Mirkin et al. ............. | 435/6 |
| 2003/0148282 A1 | 8/2003 | Mirkin et al. ............. | 435/6 |
| 2003/0207296 A1 | 11/2003 | Mirkin et al. ............. | 435/6 |
| 2003/0211488 A1 | 11/2003 | Mirkin et al. ............. | 435/6 |
| 2004/0038255 A1 | 2/2004 | Mirkin et al. ............. | 435/6 |
| 2004/0053222 A1 | 3/2004 | Mirkin et al. ............. | 435/6 |
| 2004/0072231 A1 | 4/2004 | Mirkin et al. ............. | 435/6 |
| 2004/0086897 A1 | 5/2004 | Mirkin et al. ............. | 435/6 |
| 2004/0101889 A1 | 5/2004 | Mirkin et al. ............. | 435/6 |

FOREIGN PATENT DOCUMENTS

| | | |
|---|---|---|
| EP | 0 667 398 A2 | 8/1995 |
| WO | WO 89/06801 | 7/1989 |
| WO | WO 90/02205 | 3/1990 |
| WO | WO 92/04469 | 3/1992 |
| WO | WO 93/10564 | 5/1993 |
| WO | WO 93/25709 | 12/1993 |
| WO | WO 94/29484 | 12/1994 |
| WO | WO 95/22639 | 8/1995 |
| WO | WO 97/40181 | 10/1997 |
| WO | WO 98/04740 | 2/1998 |
| WO | WO 98/10289 | 3/1998 |
| WO | WO 98/17317 | 4/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 00/25136 | 5/2000 |
| WO | WO 01/00876 | 1/2001 |
| WO | WO 01/06257 | 1/2001 |
| WO | WO 01/51665 | 7/2001 |
| WO | WO 01/73123 | 10/2001 |
| WO | WO 01/86301 | 11/2001 |
| WO | WO 02/04681 | 1/2002 |
| WO | WO 02/18643 | 3/2002 |
| WO | WO 00/33079 | 6/2002 |
| WO | WO 02/46472 | 6/2002 |
| WO | WO 02/46483 | 6/2002 |
| WO | WO 02/36169 | 10/2002 |
| WO | WO 02/079490 A3 | 10/2002 |
| WO | WO 02/096262 A2 | 12/2002 |
| WO | WO 2003/008539 A3 | 1/2003 |
| WO | WO 2003/035829 A3 | 5/2003 |
| WO | WO 2003/081202 A3 | 10/2003 |
| WO | WO 2003/087188 A1 | 10/2003 |
| WO | WO 2003/095973 A2 | 11/2003 |
| WO | WO 2004/004647 A3 | 1/2004 |
| WO | WO 2004/053105 A2 | 6/2004 |

OTHER PUBLICATIONS

Averitt, R.D. et al., "Plasmon Resonance Shifts of Au-coated Au2S Nanoshells: Insight into Multicomponent Nanoparticle Growth", Phys. Rev. Letters, vol. 78, pp. 4217-4220, 1997).*

O.D. Velev, et al., "In Situ Assembly of Collordal Particles into Miniaturized Biosensors," *Langmuir*, vol. 15, No. 11, pp. 3693-3698, May 25, 1999.

Stimpson, et al., "Real-time detection of DNA hybridization and melting on oligonucleotide arrays by using optical wave guides," *Proc. Natl. Acad. Sci..*, vol. 92, pp. 6379-6383, California Institute of Technology (1995) U.S.

Storhoff, et al., "Strategies for Organizing Nanoparticles into Aggregate Structures and Functional Materials," *Journal of Cluster Science*, vol. 8, No. 2, pp. 179-217, Plenum Publishing Corporation (1997) U.S.

Storhoff, et al., "One-Pot Colorimetric Differentiation of Polynucleotides with Single Base Imperfections Using Gold Nanoparticle Probes," *J. Am. Chem. Soc.*, vol. 20, pp. 1961-1964, American Chemical Society (1998) U.S.

Zhu, et al., "The First Raman Spectrum of an Organic Monolayer on a High-Temperature Superconductor: Direct Spectroscopic Evidence for a Chemical Interaction between an Amine and $Yba_2Cu_3O_{7-\delta}$," *J. Am. Chem. Soc.*, vol. 119, pp. 235-236, American Chemical Society (1997) U.S.

Yguerabide, et al., " Light-Scattering Submicroscopic Particles as Highly Fluorescent Analogs and Their Use as Tracer Labels in Clinical and Biological Applications," I. Theory, *Analytical Biochemistry*, vol. 262, pp. 137-156 (1998) U.S.

Yguerabide, et al., "Light-Scattering Submicroscopic Particles as Highly Fluorescent Analogs and Their Use as Tracer Labels in Clinical and Biological Applications," II. Experimental Characterization, *Analytical Biochemistry*, vol. 262, pp. 157-176 (1998) U.S.

Brada, et al., "Golden Blot"—Detection of Polyclonal and Monoclonal Antibodies Bound to Antigens on Nitrocellulose by Protein A-Gold Complexes, *Analytical Biochemistry*, vol. 42, pp. 79-83 (1984) U.S.

Dunn, et al., A Novel Method to Map Transcripts: Evidence for homology between an Adenovirus mRNA and Discrete Multiple Regions of the Viral Genome, *Cell*, vol. 12, pp. 23-36, (1997) U.S.

Hacker, High performance Nanogold—Silver in situ hybridisation, *Eur. J. Histochem*, vol. 42, pp. 111-120 (1998) U.S.

Ranki, et al., "Sandwich hybridization as a covenient method for the detection of nucleic acids in crude samples," *Gene*, vol. 21, pp. 77-85 (1983) U.S.

Romano, et al., "An antiglobulin reagent labelled with colloidal gold for use in electron microscopy," *Immunochemistry*, vol. 11, pp. 521-522 (1974) Great Britain.

Alivisatos et al., "Organization of 'nanocrystal molecules' using DNA," *Nature*, vol. 382, pp. 609-611 (1996).

Bain, et al., "Modeling Organic Surfaces with Self-Assembled Monolayers," *Angew. Chem. Int. Ed. Engl.*, vol. 28, pp. 506-512 (1989).

Bradley, "The Chemistry of Transition Metal Colloids," *Clusters and Colloids: From Theory to Applications*, G. Schmid, Editor, BCH, Weinheim, New York, pp. 459-542 (1994).

Brust et al., "Novel Gold-Dithiol Nano-Networks with Non-Metallic Electronic Properties," *Adv. Mater.*, vol. 7, pp. 795-797 (1995).

Chen et al., "A Specific Quadrilateral Synthesized from DNA Branched Junctions," *J. Am. Chem. Soc.*, vol. 111, pp. 6402-6407 (1989).

Chen & Seeman, "Synthesis from DNA of a molecule with the connectivity of a cube," *Nature*, vol. 350, pp. 631-633 (1991).

Chen et al., Crystal Structure of a Four-Stranded Intercalated DNA: $d(C_4)^{†‡}$ *Biochem.*, vol. 33, pp. 13540-13546 (1994).

Dagani, "Supramolecular Assemblies DNA to organize gold nanoparticles," *Chemical & Engineering News*, p. 6-7, Aug. 19, 1996.

Dubois & Nuzzo, "Synthesis, Structure, and Properties of Model Organic Surfaces," *Annu. Rev. Phys. Chem.*, vol. 43, pp. 437-464 (1992).

Elghanian et al., "Selective Colorimetric Detection of Polynucleotides Based on the Distance-Dependent Optical Properties of Gold Nanoparticles," *Science*, vol. 277, pp. 1078-1081 (1997).

Grabar et al., "Preparation and Characterization of Au Colloid Monolayers," *Anal. Chem.* vol. 67, pp. 735-743 (1995).

Hacia et al., "Detection of heterozygous mutations in BRCA1 using high density oligonucleotide arrays and two-colour fluorescence analysis," *Nature Genet.*, vol. 14, pp. 441-447 (1996).

Jacoby, "Nanoparticles change color on binding to nucleotide target," *Chemical &Engineering News*, p. 10, Aug. 25, 1997.

Letsinger et al., Use of Hydrophobic Substituents in Controlling Self-Assembly of Oligonucleotides, *J. Am. Chem. Soc.*, vol. 115, pp. 7535-7536 (1993).

Letsinger et al., "Control of Excimer Emission and Photochemistry of Stilbene Units by Oligonucleotide Hybridization," *J. Am. Chem. Soc.*, vol. 116, pp. 811-812 (1994).

Marsh et al., "A new DNA nanostructure, the G-wire, imaged by scanning probe microscopy," *Nucleic Acids Res.*, vol. 23, pp. 696-700 (1995).

Mirkin, "H-DNA and Related Structures," *Annu. Review Biophys. Biomol. Struct.*, vol. 23, pp. 541-576 (1994).

Mirkin et al., "A DNA-based method for rationally assembling nanoparticles into macroscopic materials," *Nature*, vol. 382, pp. 607-609 (1996).

Mirkin et al., "DNA-Induced Assembly of Gold Nanoparticles: A Method for Rationally Organizing Colloidal Particles into Ordered Macroscopic Materials," Abstract 249, Abstracts of Papers Part 1, 212 ACS National Meeting 0-8412-3402-7, American Chemical Society, Orlando, FL, Aug. 25-29, 1996.

Mucic et al., "Synthesis and characterizations of DNA with ferrocenyl groups attached to their 5'-termini: electrochemical characterization of a redox-active nucleotide monolayer," *Chem. Commun.*, pp. 555-557 (1996).

Mulvaney, "Surface Plasmon Spectroscopy of Nanosized Metal Particles," *Langmuir*, vol. 12, pp. 788-800 (1996).

Rabke-Clemmer et al., "Analysis of Functionalized DNA Adsorption on Au(111) Using Electron Spectroscopy," *Langmuir*, vol. 10, pp. 1796-1800 (1994).

Roubi, "MOLECULAR MACHINES—Nanodevice with rotating arms assembled from synthetic DNA," *Chemical & Engineering News*, p. 13, (Jan. 1999).

Seeman et al., "Synthetic DNA knots and catenanes," *New J. Chem.*, vol. 17, pp. 739-755 (1993).

Shaw & Wang, "Knotting of a DNA Chain During Ring Closure," *Science*, vol. 260, pp. 533-536 (1993).

Shekhtman et al., "Sterostructure of replicative DNA catenanes from eukaryotic cells," *New J. Chem.* vol. 17, pp. 757-763 (1993).

Smith and Feigon, "Quadruplex structure of Oxytricha telomeric DNA oligonucleotides," *Nature*, vol. 356, pp. 164-168 (1992).

Thein et al., "The use of synthetic oligonucleotides as specific hybridization probes in the diagnosis of genetic disorders," 2nd Ed., K.E. Davies, Ed., Oxford University Press, Oxford, New York, Tokyo, p. 21-33 (1993).

Wang et al., "Assembly and Characterization of Five-Arm and Six-Arm DNA Brached Junctions," *Biochem.*, vol. 30, pp. 5667-5674 (1991).

Wang et al., "A DNA Aptamer Which Binds to and Inhibits Thrombin Exhibits a New Structural Motif for DNA,"*Biochem.*, vol. 32, pp. 1899-1904 (1993).

Weisbecker et al., "Molecular Self-Assembly of Aliphatic Thiols on Gold Colloids,"*Langmuir*, vol. 12, pp. 3763-3772 (1996).

Wells, "Unusual DNA Structures," *J. Biol. Chem.*, vol. 263, pp. 1095-1098 (1988).

Zhang et al., "Informational Liposomes: Complexes Derived from Cholesteryl-conjugated Oligonucleotides and Liposomes," *Tetrahedron Lett.*, vol. 37, pp. 6243-6246 (1996).

Borman, *Chem.Eng. News*, Dec. 9, 1996, pp. 42-43 (1996).

Tomlinson et al., *Anal. Biochem*, vol. 171, pp. 217-222 (1998).

Chan, W. C. W., et al., "Quantum Dot Bioconjugates for Ultrasensitive Nonisotopic Detection," *Science*, vol. 281, p. 2016-2018, (1998).

He, L., et al., "Colloidal Au-Enhanced Surface Plasmon Resonance for Ultrasensitive Detection of DNA Hybridization," *Journal of the American Chemical Society*, vol. 122, p. 9071-9077, (2000).

Link, S., "Alloy Formation of Gold-Silver Nanoparticles and the Dependence of the Plasmon Absorption on Their Composition," *Journal of Physical Chemistry B*, , 103, 3529, (1999).

Mann, S., et al., "Biologically Programmed Nanoparticle Assembly," *Advanced Materials.*, vol. 12, p. 147-150, (2000).

Martin, B. R., et al., "Orthogonal Self-Assembly on Colloidal Gold-Platinum Nanorods," *Advanced Materials*, vol. 11, p. 1021-1025, 1999.

Mattoussi, H., et al., "Self-assembly of CdSe-ZnS quantum dot bioconjugates using an engineered recombinant protein," *Journal of the American Chemical Society*, vol. 122, p. 12142-12150, 2000.

Mitchell, G. P., et al., "Programmed assembly of DNA functionalized quantum data," *Journal of the American Chemical Society*, vol. 121, p. 8122-8123, 1999.

Mulvaney, P., et al., "Electrochemistryt of Multilayer Colloids: Preparation and Absorption Spectrum of Gold-Coated Silver Particles," *Journal of Physical Chemistry*, , vol. 97, p. 7061-7064, 1993.

Niemeyer, C. M., et al., "Covalent DNA—streptavidin conjugates as building blocks for novel biometallic nanostructures," *Angewandte Chemie International Edition in English*, , vol. 37, p. 2265-2268, 2000.

Pathak, S., et al., "Hydroxylated quantum dots as luminescent probes for in situ hybridization," *Journal of the American Chemical Society*, vol. 123, p. 4103-4104, 2001.

Rivas, L., et al., "Mixed Silver/Gold Colloids: A Study of Their Formation, Morphology and Surface-enhanced Raman Activity," *Langmuir*, vol. 16, p. 9722-9728, 2000.

Schrock. E., et al., "Multicolor spectral karyotyping of human chromosomes," *Science*, , vol. 273, p. 494-497, 1996.

Taton, T. A., "Scanometric DNA array detection with nanoparticle probes," *Science*, vol. 289, p. 1757-1760, 1999.

Taton, T. A., "Two-color Labeling of Oligonucleotide Arrays Via Size-Selective Scattering of Nanoparticle Probes," *Journal of the American Chemical Society*, vol. 123, p. 5164-5165, 2001.

Ung, T., et al., "Controlled method for silica coating of silver colloids: influence of coating on the rate of chemical reactions," *Langmuir*, vol. 14, p. 3740-3748, 1998.

Letsinger, R., et al., "Chemistry of Oligonucleotide-Gold Nanoparticle Conjugates," *Phosphorus, Sulfur and Silicon*, vol. 144, p. 359-362 (1999).

Letsinger, R., et al., "Use of a Steroid Cyclic Disulfide Anchor in Constructing Gold Nanoparticle—Oligonucleotide Conjugates," *Bioconjugate Chem*, p. 289-291 (2000).

Li Z., et al., "Multiple thiol-anchor capped DNA-gold nanoparticle conjugates," *Nucleic Acids Research*, vol. 30, p. 1558-1562 (2002).

Nuzzo R., et al., "Spontaneously Organized Molecular Assemblies. 3. Preparation and Properties of Solution Adsorbed Monolayers of Organic Disulfides on Gold Surfaces," *J. Am Chem. Soc.*, vol. 109, p. 2358-2368 (1987).

Otsuka, H., et al., "Quantitative and Reversible Lectin-Induced Association of Gold Nonoparticles Modified with $^\alpha$-Lactosyl$^\omega$-mercapto-poly(ethyleneglycol)," *J. Am Chem. Soc.*, vol. 123, p. 8226-8230 (2001).

Wuelfing, P., et al., "Nanometer Gold Clusters Protected by Surface-Bound Monolayers of Thiolated Poly(ethyleneglycol) Polymer Electrolyte," *J. Am Chem. Soc.*, vol. 120, p. 12696-12697 (1998).

Mohanty J., et al. "Pulsed laser excitation of phosphate stabilized silver nanoparticles," *Proc. Indian Acd. Sci.*, vol. 112, No. 1, p. 63-72.

Nicewarner- Peña S., et al., "Hybridization and Enzymatic Extension of Au Nanoparticle-Bound Oligonucleotides," *J. Am. Chem. Soc.*, vol. 124, p. 7314-7323 (2002).

Whitesides G.M., et al., "Soft Lithography in Biology and Biochemistry," *Annu. Rev. Biomed. Eng.*, p. 335-373 (2001).

Cao, et al., "DNA-Modified Core-Shell Ag/Au Nanoparticles", *J. Am. Chem. Soc.*, vol. 123, pp. 7961-7962, 2001.

Remita, et al., "Radiolytic formation of bilayered $Pt_{core}/Au_{shell}$ and $Au_{core}/Pt_{shell}$ clusters in aqueous solution", *Radiation Physics and Chemistry*, vol. 54, pp. 463-473, 1999.

Wang, et al., "The surface chemistry of hybrid nanometer-sized particles I. Photochemical deposition of gold on ultrafine $TiO_2$ particles", *Colloids and Surfaces A: Physiochemical and Engineering Aspects*, vol. 131, pp. 271-280, 1998.

Carla M. Aguirre, Cristin E. Moran, James F. Young, and Naomi J. Halas, "*Laser-Induced Reshaping of Metallodielectric Nanoshells under Ferntosecond and Nanosecond Plasmon Resonant Illumination*", *J. Phys. Chem. B*, vol. 108, 7040-7045 (2004).

Carla M. Aguirre, Tara R. Kaspar, Corey Radloff, and Naomi J. Halas, "*CTAB Mediated Reshaping of Metallodielectric Nanoparticles*", *Nano Letters*, vol. 3, No. 12, 1707-1711 (2003).

R. D. Averitt, S. L. Westcott, and N. J. Halas, "*The ultrafast optical properties of gold nanoshells*", *J. Opt. Soc. Am. B.*, vol. 16, No. 10, 1814-1823 (1999).

R. D. Averitt, S. L. Westcott and N. J. Halas, "*Linear optical properties of gold nanoshells*", *J. Opt. Soc. Am. B.*, vol. 16, No. 10, 1824-1832 (1999).

R. D. Averitt, S. L. Westcott and N. J. Halas, "*Ultrafast Electron Dynamics in Gold Nanoshells*", *Phys. Rev. B*, vol. 58, R10203-R10206 (1998).

C. Charnay, A. Lee, S. Man, C. E. Moran, C. Radloff, R. K. Bradley, and N. J. Halas, "*Reduced Symmetry Metallodielectric Nanoparticles: Chemical Synthesis and Plasmonic Properties*", *J. Phys. Chem. B*, vol. 107, 7327-7333 (2003).

N.K. Grady, N.J. Halas, and P. Nordlander, "*Influence of dielectric function properties on the optical response of plasmon resonant metallic nanoparticles*", *Chem. Phys. Lett.*, vol. 399, 167-171 (2004).

Naomi Halas, "*The Optical Properties of Nanoshells*", *Optics and Photonics News*, 26-30 (2002).

N. J. Halas, G. D. Hale, S. J. Oldenburg, "*Dynamics of Triplet Excitons in MEH-PPV measured by Two-Photon Photoemission*," *SPIE Proceedings*, vol. 3145, pp. 229-239 (1998).

G. D. Hale, J. B. Jackson, O. E. Shmakova, T. R. Lee, and N. J. Halas, "*Enhancing the Active Lifetime of Luminescent Semiconducting Polymers Via Doping With Metal Nanoshells*", *Appl. Phys. Lett.*, vol. 78, No. 11, 1502-1504 (2001).

L. R. Hirsch, R. J. Stafford, J. A. Bankson, S. R. Sershen, B. Riveria, R. E. Price, J. D. Hazle, N. J. Halas, J. L. West, "*Nanoshell-mediated near-infrared thermal therapy of tumors under magnetic resonance guidance*", *PNAS*, vol. 100, No. 23, 13549-13554 (2003).

L. R. Hirsch, J. B. Jackson, A. Lee, N. J. Halas, and J. L. West, "*A Whole Blood Immunoassay Using Gold Nanoshells*", *Anal. Chem.*, vol. 75, 2377-2381 (2003).

L. R. Hirsch, R. J. Stafford, J. A. Bankson, S. R. Sershen, R. E. Price, J. D. Hazle, N. J. Halas, J. L. West, "*Targeted photothermal tumor therapy using metal nanoshells*", *Proceedings of the Second Joint EMBS/BMES Conference*, vol. 1, 530-531 (2002).

L. R. Hirsch, N. J. Halas, J. L. West, "A rapid, near infrared, whole blood immunoassay using metal nanoshells", *Proceedings of the Second Joint EMBS/BMES Conference*, vol. 1, 1646-1647 (2002).

J.B. Jackson and N.J. Halas, "*Surface-enhanced Raman scattering on tunable plasmonic nanoparticle substrates*", *Proc. Natl. Acad. Sci. USA*, vol. 101, No. 52, 17930-17935 (2004).

J. B. Jackson, S. L. Westcott, L. R. Hirsch, J. L. West, and N. J. Halas, "*Controlling the surface enhanced Raman effect via the nanoshell geometry*", *Appl. Phys. Lett.*, vol. 82, No. 2, 257-259 (2003).

J. B. Jackson and N. J. Halas, "*Probing the optical near field of a nanolens*", *Properties of Metal Nanostructures, Proceedings of SPIE*, vol. 4810, 82-90 (2002).

J. B. Jackson and N. J. Halas, "*Silver Nanoshells: Variations in Morphologies and Optical Properties*", *J. Phys. Chem. B*, vol. 105, 2743-2746 (2001).

K. F. Kelly, E. T. Mickelson, R. H. Hauge, J. L. Margrave, and N. J. Halas, "*Nanoscale imaging of chemical interactions: fluorine on graphite*", *Proc. Natl. Acad. Sci. U. S. A.*, vol. 97, No. 19, 10318-10321 (2000).

K. F. Kelly, I. W. Chiang, E. T. Mickelson, R. H. Hauge, J. L. Margrave, X. Wang, G. E. Scuseria, C. Radloff, N. J. Halas, "*Insight into the mechanism of sidewall functionalization of single-walled nanotubes : an STM study*," *Chem. Phys. Lett.*, vol. 313, 445-450 (1999).

S. Lal, R. N. Taylor, J. B. Jackson, S. L. Westcott, P. Nordlander, and N. J. Halas, "*Light Interaction between Gold Nanoshells Plasmon Resonance and Planar Optical Waveguides*", *J. Phys. Chem. B.*, vol. 106, 5609-5612 (2002).

Yu Liu, Valery N. Khabashesku, and Naomi Halas, "*Fluorinated Nanodiamond as a Wet Chemistry Precursor for Diamond Coatings Covalently Bonded to Glass Surface*", *J. Am. Chem. Soc.*, vol. 127, 3712-3713 (2005).

Christopher Loo, Amanda Lowery, Naomi Halas, Jennifer West, and Rebekah Drezek, "*Immunotargeted Nanoshells for Integrated Cancer Imaging and Therapy*", *Nano Letters*, vol. 5, No. 4, 709-711 (2005).

Christopher Loo, B.S., Alex Lin, B.S., Leon Hirsch, B.S., Min-Ho Lee, M.S., Jennifer Barton, Ph.D., Naomi Halas, Ph.D., Jennifer West, Ph.D., Rebekah Drezek, Ph.D., "*Nanoshell-Enabled Photonics-Based Imaging and Therapy of Cancer*", *Technology in Cancer Research and Treatment*, vol. 3, 33-40 (Feb. 2004).

C. E. Moran, C. Radloff, and N. J. Halas, "*Benchtop Fabrication of Submicrometer Metal Line and Island Arrays Using Passivative Microcontact Printing and Electroless Plating*", *Adv. Mater.*, vol. 15, No. 10, 804-807 (2003).

C. E. Moran, J. M. Steele, A. Lee, C. Aguirre, C. Radloff, A. Rimberg, and N. J. Halas, "*Soft lithographic directed growth of wire grating arrays resonances*", *Properties of Metal Nanostructures, Proceedings of SPIE*, vol. 4810, 1-6 (2002).

C. E. Moran, G. D. Hale and N. J. Halas, "*Synthesis and Charcterization of Lanthanide-Doped Silica Microspheres*", *Langmuir*, vol. 17, 8376-8379 (2001).

Colleen L. Nehl, Nathaniel K. Grady, Glenn P. Goodrich, Felicia Tam, Naomi J. Halas, and Jason H. Hafner, "*Scattering Spectra of Single Gold Nanoshells*", *Nano Letters*, vol. 4, 2355-2359 (2004).

S. J. Oldenburg, J. B. Jackson, S. L. Westscott, and N. J. Halas, "*Infrared Extinction Properties of Gold Nanoshells*", *Appl. Phys. Lett.*, vol. 75, No. 19, 2897-2899 (1999).

S. J. Oldenburg, G. D. Hale, J. B. Jackson, and N. J. Halas, "*Light scattering from dipole and quadrupole nanoshell antennas*", *Appl. Phys. Lett.*, vol. 75, No. 8, 1063-1065 (1999).

S. J. Oldenburg, S. L. Westcott, R. D. Averitt, and N. J. Halas, "*Surface Enhanced Raman Scattering in the Near Infrared using Metal Nanoshell Substrates*", *J. Chem. Phys.*, vol. 111, No. 10, 4729-4735 (1999).

S. Oldenburg, R. D. Averitt, S. Westcott, and N. J. Halas, "*Nanoengineering of Optical Resonances*", *Chem. Phys. Lett.*, vol. 288, 243-247 (1998).

D. Patrick O'Neal, Leon R. Hirsch, Naomi J. Hales, J. Donald Payne, Jennifer L. West, "*Photo-thermal tumor ablation in mice using near infrared-absorbing nanoparticles*", *Cancer Letters*, vol. 209, 171-176 (2004).

T. Pham, J. B. Jackson, N. J. Halas, and T. R. Lee "*Preparation and Charcterization of Gold Nanoshells Coated with Self-Assembled Monolayers*", Langmuir, vol. 18, 4915-4920 (2002).

L. A. Porter, D. Ji, S. L. Westcott, M. Graupe, R. S. Czernuszewicz, N. J. Halas, and T. R. Lee, "*Gold and Silver Nanoparticles Functionalized by the Adsorption of Dialkyl Disulfides*", Langmuir, vol. 14, 7378-7386 (1998).

E. Prodan, C. Radloff, N. J. Halas, P. Nordlander, "*A Hybridization Model for the Plasmon Response of Complex Nanostructures*", Science, vol. 302, 419-422 (2003).

E. Prodan, P. Nordlander, N. J. Halas, "*Electronic Structure and Optical Properties of Gold Nanoshells*", Nano Letters, vol. 3, No. 10, 1411-1415 (2003).

E. Prodan, P. Nordlander, and N. J. Halas, "*Effects of dielectric screening on the optical properties of metallic nanoshells,*" Chemical Physics Letters, vol. 368, 94-101 (2003).

C. Radloff and N. J. Halas, "*The decomposition of gold nanoshells in carbon tetrachloride*", Properties of Metal Nanostructures, Proceedings of SPIE, vol. 4810, 21-27 (2002).

C. Radloff and N. J. Halas, "*Enhanced Thermal Stability of Silica-encapsulated Metal Nanoshells*", Appl. Phys. Lett., vol. 79, No. 5, 674-676 (2001).

S. R. Sershen, S. L. Westcott, N. J. Halas, and J. L. West, "*Temperature-Sensitive Polymer-Nanoshell Composites for Photothermally Modulated Drug Delivery*", J. Biomedical Materials Research, vol. 51, 293-298 (2000).

S. R. Sershen, S. L. Westcott, N. J. Halas, J. L. West, "*Independent optically addressable nanoparticle-polymer optomechanical composites*", Appl. Phys. Lett., vol. 80, No. 24, 4609-4611 (2002).

S. R. Sershen, N. J. Halas, J. L. West, "*Pulsatile release of insulin via photothermally modulated drug delivery*", Proceedings of the Second Joint EMBS/BMES Conference, vol. 1, 490-491 (2002).

S. R. Sershen, S. L. Westcott, J. L. West, and N. J. Halas, "*An Opto-Mechanical Nanoshell-Polymer Composite*", Appl. Phys. B, vol. 73, 379-381 (2001).

D. D. Smith, L. Sibille, R. J. Cronise, A. J. Hunt, S. J. Oldensburg, D. Wolfe, and N. J. Halas, "*Effect of Microgravity on the Growth of Silica Nanostructures*", Langmuir, vol. 16, 10055-10060 (2000).

Felicia Tam, Cristin Moran, and Naomi Halas, "*Geometrical Parameters Controlling Sensitivity of Nanoshell Plasmon Resonances to Changes in Dielectric Environment*", J. Phys. Chem. B, vol. 108, 17290-17294 (2004).

F. Tam, and N. J. Halas, "*Plasmon Response of Nanoshell Dopants in Organic Films: A Stimulation Study*", Progress in Organic Coatings, vol. 47, 275-278 (2003).

West, Jennifer L., Halas, Naomi J., "*Engineered Nanoma Terials for Biophotonics Applications: Improving Sensing, Imaging, and Therapeutics*", Annual Review of Biomedical Engineering, vol. 5, 285-292 (2003).

J. L. West and N. J. Halas, "*Applications of Nanotechnology to Biotechnology—Commentary*", Current Opinion in Biotechnology, vol. 11, 215-217 (2000).

S. L. Westcott, J. B. Jackson, C. Radloff, and N. J. Halas, "*Relative Contributions to the Plasmon Line Shape of Metal Nanoshell*", Phys. Rev. B, vol. 66, 155431-1—155431-5 (2002).

S. L. Westcott and N. J. Halas, "*Electron Relaxation Dynamics in Semicontinuous Metal Films on Nanoparticle Surfaces*", Chem. Phys. Lett., vol. 356, 207-213 (2002).

S. L. Westcott, R. D. Averitt, J. A. Wolfgang, P. Nordlander, and N. J. Halas, "*Adsorbate-Induced Ouenching of Hot Electrons in Gold Core-Shell Nanoparticles*", J. Phys. Chem. B, vol. 105, No. 41, 9913-9917 (2001).

S. L. Westcott, S. J. Oldenburg, T. R. Lee and N. J. Halas, "*Construction of Simple Gold Nanoparticle Aggregates with Controlled Plasmon-Plasmon Interactions,*" Chem. Phys. Lett., vol. 300, 651-655 (1999).

S. Westcott, S. Oldenburg, T. R. Lee, and N. J. Halas, "*Formation and Adsorption of Clusters of Gold Nanoparticles onto Functionalized Silica Nanoparticle Surfaces*", Langmuir, vol. 14, 5396-5401 (1998).

D. B. Wolfe, S. J. Oldenburg, S. L. Westcott, J. B. Jackson, M. S. Paley, and N. J. Halas, "*Preparation and characterization of polymer-coated nanoparticles,*" SPIE Proceedings, vol. 3793, 129-137 (1999).

C. Radloff, C.E. Moran, J.B. Jackson and N.J. Halas, "Nanoparticles: Building Blocks for Functionalized Nanostructures" in *Molecular Nanoelectronics*, Mark Reed and Takhee Lee, eds., American Scientific Publishers (2003).

Cao et al., "*DNA-Modified Core-Shell Ag/Au Nanoparticles*", J. Am. Chem. Soc., 2001, 123, 7961-7962.

Remita et al., "*Radiolytic formation of bilayered $Pt_{core}/Au_{shell}$ and $Au_{core}/Pt_{shell}$ clusters in aqueous solution*", Radiation Physics and Chemistry, 54 (1999) 463-473.

Wang et al., "*The surface chemistry of hybrid nanometer-sized particles I. Photochemical deposition of gold on ultrafine $TiO_2$ particles*", Colloids and Surfaces A: Physiochemical and Engineering Aspects, 131 (1998) 271-280.

\* cited by examiner

CORESHELL APPROACH TO MAGNETIC GOLD NANOPARTICLES

GOLD CO.
MAGNETIC NAN

A: METAL OXIDES MAGNETIC CORES: $Fe_3O_4, Co_3O_4$
B: PURE METAL CORES: Fe, Co, Ni ...
C: ALLOY METAL CORES: FePt, FeAu

MAGNETIC PROPERTIES OF GOLD COATED
$Fe_3O_4$ NANOPARTICLES

WITHOUT A MAGNETIC FIELD

WITH THE COLOR OF
GOLD NANOPARTICLES

IN A MAGNETIC FIELD FOR 12 HRS

COLORLESS

SEQUENCE LISTING

```
<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 1
taacaataat ccctcaaaaa aaaaaaaaaa aaaaa                              35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 2
aaaaaaaaaa aaaaaaaaaa atccttatca atatt                              35

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 3
gagggattat tgttaaatat tgataaggat                                    30
```

NON-ALLOYING CORE SHELL NANOPARTICLES

CROSS-REFERENCE

This application is a continuation-in-part of U.S. application Ser. No. 10/034,451, filed Dec. 28, 2001 and PCT/US01/50825, filed Dec. 28, 2001. This application claims the benefit of priority from U.S. Provisional application No. 60/293,861, filed May 25, 2001, which is incorporated by reference in its entirety.

The work reported in this application has been supported, in part, by NSF grant no. CHE-9871903; ARO grant no. DAAG55-97-1-0133, and AFOSR grant no. DURINT. Accordingly, the U.S. government may have some rights to the invention.

FIELD OF INVENTION

The present invention relates to core/shell nanoparticles, materials based on core/shell nanoparticles, kits containing core/shell nanoparticles, and methods of making and using core/shell nanoparticles for the detection of target molecules, including nucleic acids, peptides, and proteins. In particular, the present invention relates to DNA-modified core/shell nanoparticles and their use for detecting target molecules such as nucleic acids.

BACKGROUND OF INVENTION

In 1996, a method was reported for utilizing biomolecules, such as DNA, and their molecular recognition properties to guide the assembly of nanoparticle building blocks modified with complementary recognition elements into functional materials.[1] These materials have found wide application in the development of highly sensitive and selective diagnostic methods for DNA.[2] This material synthesis approach has been extended to a wide range of biomolecules, including peptides and proteins,[3] and a modest collection of nanoparticles including gold and semiconductor quantum dots.[4-9] In each case, when a new nanoparticle composition is designed, new modification methods must be developed for immobilizing biomolecules on the surface of the particles of interest. This approach has been extensively utilized but with limited success. The methods for modifying gold nanoparticles have now been optimized and generalized for a wide range of particle sizes and surface compositions, including spheres and rods.[1,2,4,10] Gold particles are particularly easy to modify because they are often stabilized with a weakly binding layer of charged ligands (e.g. citrate) that can be replaced with molecules with chemical functionalities that bind more strongly (e.g. thiols, amines, and disulfides) to their surfaces than these ligands. The CdSe and CdS quantum dots have proven more difficult to modify because they have a surfactant layer that is very strongly bound to their surfaces and, consequently, difficult to displace.[5] No successful routes have been developed for creating stable oligonucleotide conjugates with silver nanoparticles, primarily because they tend to chemically degrade under conditions used to effect DNA hybrization. A major advance would be to devise a method for designing particles with the physical properties of a chosen nanoparticle composition but the surface chemistry of gold. Herein, a low temperature method is provided for generating core/shell particles consisting of a silver core and a non-alloying gold shell that can be readily functionalized with oligonucleotides using the proven preparatory methods for pure gold particle oligonucleotide conjugates.[2d] Moreover, the novel nanoparticle composition can be used to access a colorimetric detection system distinct from the pure gold system.[2a,2d]

BRIEF SUMMARY OF THE INVENTION

The present invention relates to composite core/shell nanoparticles, compositions and kits including these core/shell nanoparticles, and methods for preparing and using composite core/shell nanoparticles, particularly Ag/gold core/shell nanoparticles, for the detection of target molecules such as nucleic acids, proteins and the like. These Ag/gold core/shell nanoparticles were prepared by reduction of $HAuCl_4$ by $NaBH_4$ in the presence of Ag-nanoparticle "templates" and characterized by UV-vis spectroscopy, transmission electron microscopy (TEM), and energy dispersive X-ray (EDX) microanalysis. Significantly, these particles do not alloy, yielding structures with the optical properties of silver and the surface chemistry and high stability of Au. Experimental and theoretical data support the structural characterization of these novel materials as silver cores (~12 nm in diameter) coated with approximately one atomic monolayer of gold (~3 Å). The core/shell nanoparticles may be further modified with alkanethiol-oligonucleotides forming structures that undergo reversible hybridization with complementary oligonucleotides to form extended nanoparticle network structures. By spotting aliquots of a solution containing the oligonucleotide-modified nanoparticles without and with DNA target on a reverse-phase alumina plate, a distinct calorimetric transition from yellow to dark brown can be observed by the naked eye. The optical properties of the dispersed and aggregated core/shell particles form a new calorimetric channel for nanoparticle based DNA detection.

Accordingly, one object of the invention is to provide straightforward method of preparing core/shell nanoparticles with the optical, and many of the physical, properties of silver but the stability of gold. The surfaces of these nanoparticles can be modified with a variety of moieties such as, for example, natural and synthetic polymers, molecules capable of selective molecular recognition including, but not limited to, nucleotides, nucleosides, poly- or oligonucleotides, proteins, peptides, carbohydrates, sugars, and haptens, thereby providing useful biorecognition properties to the nanoparticles.

Another object of the invention is to provide a general method for preparing core/shell particles with tailorable physical properties by virtue of choice of core, e.g., $Fe_3O_4$, CdS, CdSe, Ag—Au alloy, Co, Cu or Pt, but the surface chemistry and stability of the native, and oligonucleotide modified, pure gold particles.

Another object of the invention is to provide methods for detection of molecules capable of selective molecular recognition comprising use of core/shell nanoparticle probes. These methods comprise contacting the core/shell nanoparticle probes with one or a plurality of target molecules under conditions that allow for selective molecular recognition, and the detection of an optical change. The physical properties of the particular core/shell nanoparticle probes can allow for various additional steps in these methods such as, for example, inducing their migration through application of electrical or magnetic fields.

Another object of the invention is to provide nanomaterials based on the core/shell nanoparticles of the invention.

These and other objects of the invention will become apparent in light of the detailed description below.

DETAILED DESCRIPTION OF THE INVENTION

Figure 1A:
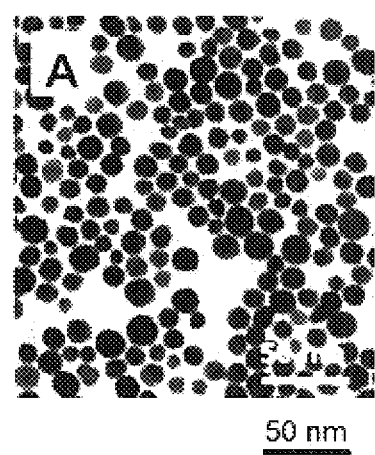
FIG. 1 illustrates (A) a TEM image of Ag/gold core/shell nanoparticles; (B) EDX spectra of silver core nanoparticles (dotted line) and silver/gold core/shell nanoparticles (solid line) wherein L and M signify electron transitions into the L and M shell of the atoms, respectively, from higher states; (C) UV-vis spectra of silver core (dotted line) and Ag/gold core/shell (solid line) wherein the inset shows the calculated extinction spectra of silver nanoparticles (dotted line) and Ag/gold core/shell nanoparticles (solid line); (D) Thermal denaturization curve of aggregates formed from hybridized oligonucleotide modified Ag/gold core/shell nanoparticles in buffer solution (0.3 M NaCl and 10 mM phosphate buffer, pH=7). The inset shows the UV-vis spectra of dispersed oligonucleotide-modified Ag/gold core/shell nanoparticles (solid line) and aggregated (dotted line) oligonucleotide-modified Ag/gold core/shell nanoparticles formed via hybridization. The base sequences are given in FIG. 2A.

In one aspect the present invention provides for core/shell nanoparticles, comprising a nanoparticle core and a gold shell. The core material can comprise any nanoparticle known to those of skill in the art including, but not limited to, metal, semiconductor, and magnetic nanoparticles. In a preferred embodiment, the core material is comprised of metal or magnetic nanoparticles including, but not limited to, Ag, Pt, Fe, Co, Ni, FePt, FeAu, $Fe_3O_4$, $Co_3O_4$ and CdSe (or CdS). Methods for preparing such nanoparticles are well known in the art. For example, see, e.g. Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988).

In yet another aspect the present invention provides a method for preparation of non-alloying gold core/shell nanoparticles and product produced therefrom. The method of the invention comprises providing an inner nanoparticle core, treating the core simultaneously with a solution comprising a gold salt and a solution comprising a reducing agent, and isolating the core/shell nanoparticles. The method provides for the first time a non-alloying gold shell surrounding a nanoparticle core. These non-alloying gold core/shell nanoparticles exhibit surprising superior spectroscopic properties not found in conventional gold core/shell nanoparticles and can be functionalized with molecules such as nucleic acids and receptors, to produce nanoparticle conjugates that can be used for targeting and detecting target analytes such as nucleic acids, antigens, proteins, carbohydrates and other substances.

In practicing the method of the invention, the method can be performed at any temperature favorable in producing a non-alloying gold shell surrounding the core. Generally, the temperature depends on the choice of reaction solvent used to generate the gold shell. Suitable, but non-limiting, examples of reaction solvents include water, ethanol, methanol, trisodium citrate solution, oleic acid, trioctylphosphine oxide, and trioctylphosphine. In practicing this invention, trisodium citrate solution (0.3 mM) is preferred.

In practicing the method of the invention, the temperature generally ranges from about 0° C. to about 45° C. in water or aqueous reaction solutions. For organic solvents, the temperature generally ranges from about 130° C. to about 180° C. when oleic acid and trioctylphosphine oxide are used.

The gold salt can comprise any suitable gold salt including, but not limited to, $HAuCl_4$, $NaAuCl_4$, $KAuCl_4$, or $KAu(CN)_2$. In practicing the invention, the preferred gold salt is $HAuCl_4$.

The reducing agent can comprise any suitable reducing agent capable of reducing the valency of the gold that comprises the gold salt solution including, but not limited to, $NaBH_4$, ascorbic acid, $NH_2OH$ and $N_2H_4$. In practicing the invention, the preferred reducing agent is $NaBH_4$.

In another aspect, the present invention provides for core/shell nanoparticle oligonucleotide conjugates, comprising a nanoparticle core, a gold shell surrounding the nanoparticle, and an oligonucleotide attached to the gold surface of the core/shell nanoparticle. The size of the nanoparticles is preferably from about 5 nm to about 150 nm (mean diameter), more preferably from about 5 to about 50 nm, most preferably from about 10 to about 30 nm. Any suitable method for attaching oligonucleotides onto a gold surface may be used. A particularly preferred method for attaching oligonucleotides onto a gold surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820, 279, filed Mar. 28, 2001; Ser. No. 09/927,777, filed Aug. 10, 2001; and in International application nos. WO 98/04740, filed Jul. 21, 1997; WO 01/00876, filed Jun. 26, 2000; WO 01/51665, filed Jan. 12, 2001; WO 01/73123, filed Mar. 28, 2001, the disclosures which are incorporated by reference in their entirety. The aging process provides nanoparticle-oligonucleotide conjugates with unexpected enhanced stability and selectivity. The method comprises providing oligonucleotides preferably having covalently bound thereto a moiety comprising a functional group which can bind to the nanoparticles. The moieties and functional groups are those that allow for binding (i.e., by chemisorption or covalent bonding) of the oligonucleotides to nanoparticles. For instance, oligonucleotides having an alkanethiol, an alkanedisulfide or a cyclic disulfide covalently bound to their 5' or 3' ends can be used to bind the oligonucleotides to a variety of nanoparticles, including gold nanoparticles.

The oligonucleotides are contacted with the nanoparticles in water for a time sufficient to allow at least some of the oligonucleotides to bind to the nanoparticles by means of the functional groups. Such times can be determined empirically. For instance, it has been found that a time of about 12–24 hours gives good results. Other suitable conditions for binding of the oligonucleotides can also be determined empirically. For instance, a concentration of about 10–20 nM nanoparticles and incubation at room temperature gives good results.

Next, at least one salt is added to the water to form a salt solution. The salt can be any suitable water-soluble salt. For instance, the salt may be sodium chloride, lithium chloride, potassium chloride, cesium chloride, ammonium chloride, sodium nitrate, lithium nitrate, cesium nitrate, sodium acetate, lithium acetate, cesium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time has been found to give the highest surface density of oligonucleotides on the nanoparticles. Suitable ionic strengths can be determined empirically for each salt or combination of salts. A final concentration of sodium chloride of from about 0.1 M to about 1.0 M in phosphate buffer, preferably with the concentration of sodium chloride being increased gradually over time, has been found to give good results.

After adding the salt, the oligonucleotides and nanoparticles are incubated in the salt solution for an additional period of time sufficient to allow sufficient additional oligonucleotides to bind to the nanoparticles to produce the stable nanoparticle-oligonucleotide conjugates. As will be described in detail below, an increased surface density of the oligonucleotides on the nanoparticles has been found to stabilize the conjugates. The time of this incubation can be determined empirically. A total incubation time of about 24–48, preferably 40 hours, has been found to give good results (this is the total time of incubation; as noted above, the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results.

The conjugates produced by use of the "aging" step have been found to be considerably more stable than those produced without the "aging" step. As noted above, this increased stability is due to the increased density of the oligonucleotides on the surfaces of the nanoparticles which is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. Preferably, the surface density is at least 15 picomoles/cm$^2$. Since the ability of the oligonucleotides of the conjugates to hybridize with nucleic acid and oligonucleotide targets can be diminished if the surface density is too great, the surface density is preferably no greater than about 35–40 picomoles/cm$^2$.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

In yet a further aspect the invention provides methods for the detection of a target analytes such as nucleic acids comprising contacting the core/shell nanoparticle oligonucleotide conjugates of the instant invention with a target nucleic acid sequence under conditions that allow hybridization between at least a portion of the oligonucleotides bound to the nanoparticle and at least a portion of the target nucleic acid sequence. In addition, protein receptors and other specific binding pair members can be functionalized with oligonucleotides and immobilized onto oligonucleotide-modified nanoparticles to generate a new class of hybrid particles (nanoparticle-receptor conjugates) that exhibit the high stability of the oligonucleotide modified particles but with molecular recognition properties that are dictated by the protein receptor rather than DNA. Alternatively, one could functionalize a protein that has multiple receptor binding sites with receptor-modified oligonucleotides so that the protein receptor complex could be used as one of the building blocks, in place of one of the inorganic nanoparticles, in the original nanomaterials assembly scheme discussed above. The use of these novel nanoparticle-receptor conjugates in analyte detection strategies have been evaluated in a number of ways including identification of targets and screening for protein-protein interactions. For suitable hybridization conditions for nucleic acid detection, and methods for preparing nanoparticle-receptor conjugates are described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. WO 98/04740, filed Jul. 21, 1997; WO 01/00876, filed Jun. 26, 2000; WO 01/51665, filed Jan. 12, 2001; WO 01/73123, filed Mar. 28, 2001, the disclosures which are incorporated by reference in their entirety. Once a core/shell nanoparticle conjugate of the invention binds to a target molecule, a change in the optical characteristics of the core/shell nanoparticle conjugates can be readily detected. In another embodiment the detection step is performed in the presence of an applied magnetic field which further enhances hybridization or binding of the nanoparticle conjugate with the target molecule such as a nucleic acid.

The invention further provides a method of nanofabrication based on the core-shell nanoparticle conjugates of the invention. Nanostructures and methods for prepare the materials from nanoparticles have been described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. WO 98/04740, filed Jul. 21, 1997; WO 01/00876, filed Jun. 26, 2000; WO 01/51665, filed Jan. 12, 2001; WO 01/73123, filed Mar. 28, 2001, the disclosures which are incorporated by reference in their entirety. The method comprises providing at least one type of linking oligonucleotide having a selected sequence, the sequence of each type of linking oligonucleotide having at least two portions. The method further comprises providing one or more types of core/shell nanoparticles having oligonucleotides attached thereto, the oligonucleotides on each type of nanoparticles having a sequence complementary to a portion of the sequence of a linking oligonucleotide. The linking oligonucleotides and nanoparticles are contacted under conditions effective to allow hybridization of the oligonucleotides on the nanoparticles to the linking oligonucleotides so that a desired nanomaterials or nanostructure is formed.

The invention provides another method of nanofabrication. This method comprises providing at least two types of core-shell nanoparticles of the invention having oligonucleotides attached thereto. The oligonucleotides on the first type of nanoparticles have a sequence complementary to that of the oligonucleotides on the second type of nanoparticles. The oligonucleotides on the second type of nanoparticles have a sequence complementary to that of the oligonucleotides on the first type of nanoparticle-oligonucleotide conjugates. The first and second types of nanoparticles are contacted under conditions effective to allow hybridization of the oligonucleotides on the nanoparticles to each other so that a desired nanomaterials or nanostructure is formed.

The invention further provides nanomaterials or nanostructures composed of core-shell nanoparticles having oligonucleotides attached thereto, the nanoparticles being held together by oligonucleotide connectors.

The following examples serve to illustrate certain embodiments of the present invention, and do not limit it in scope or spirit. Certain obvious alternatives and variations will be apparent to those of skill in the art.

EXAMPLE 1

Synthesis of Ag/gold Core/shell Nanoparticles Prepared Via a Two-step Synthesis

This Example illustrates the inventive process for preparing Ag/gold core/shell nanoparticles. In part A, methods for preparing silver cores are described. In part B, a method for preparing Ag/gold core/shell nanoparticles is provided. Silver nanoparticles are desired compositions for building blocks in material synthesis and as biological labels for two important reasons: (1) silver particles exhibit a surface plasmon band between ~390 and 420 nm, depending on the particle size;[11] this is a spectral regime that is distinct from that of gold (520–580 nm). (2) The extinction coefficient of the surface plasmon band for an silver particle is approximately 4 times as large as that for an gold particle of the same size.[12] Therefore, silver particles functionalized with DNA would provide not only an opportunity to tailor the optical properties of DNA/nanoparticle composite structures but also routes to new diagnostic systems that rely on the position and intensity of the surface plasmon band (e.g. colorimetric systems based on absorption or scattering, or SPR and SERS detection systems).

Experimentally, it has been determined that silver nanoparticles cannot be effectively passivated by alkylthiol-modified-oligonucleotides using the established protocols for modifying goldparticles.[2] Indeed, silver particle-DNA conjugate prepared via such methods irreversibly aggregate when heated in a solution with a salt concentration necessary to effect DNA hybridization (0.05 M NaCl or greater). Herein, a core/shell approach was applied to overcome this problem. In this approach, a thin gold shell was grown upon an silver nanoparticle, forming a particle with an gold outer surface that can be easily modified with alkylthiol-oligonucleotides. This approach could be generalized to prepare other particles such as Cu and Pt to create a series of core/shell particles with tailorable physical properties by virtue of choice of core but the surface chemistry and stability of the native, and oligonucleotide modified, pure gold particles.

A. Preparation of Silver Nanoparticle Cores

Silver nanoparticles were synthesized silver nanocrystals by reduction of silver nitrate by sodium borohydride in a trisodium citrate solution. Two methods for synthesizing the silver nanocrystals are described below and the resulting core nanocrystals were compared.

Method No. 1: $AgNO_3$ (2.2 mg) and sodium citrate dihydrate (8.2 mg) were dissolved in 99 ml of Nanopure water in a 250-ml flask. With stirring and under Ar, this flask was placed in a ice bath for 15 min. Then 1 ml of sodium borohydride solution (0.14 M) was injected into the solution. After stirring for 1 hr, the solution was warmed to room temperature. The silver nanoparticles (~12 nm in diameter) were obtained. Without further purification, these silver nanoparticles could be directly used for the gold shell growth.

Method No. 2: $AgNO_3$ (2.2 mg) and sodium citrate dihydrate (8.2 mg) were dissolved in 98 ml of Nanopure water in a 250-ml flask. With stirring and under an Ar atmosphere, this flask was placed in an ice bath for 15 min. Then 1 ml of sodium borohydride solution (0.14 M) was injected into the solution. After stirring for 1 hr, the solution was warmed to room temperature. The Ag nanoparticles (~12 nm in diameter) were obtained. Bis(p-sulfonatophehyl)-phenylphosphine (BSPP, 17 mg) was put into the silver nanoparticle solution and stirred overnight. The silver nanoparticles are subsequently purified and isolated by gradient centrifugation between 12 kRPM~20 kRPM. The resulting silver nanoparticle-containing aliquots from the precipitation are combined, and dispersed in Nanopure water.

Comparison results: silver particles prepared by method no. 2 have better size distribution compared with those prepared by method no. 1 ($\sigma=18\%$ for method no. 2; $\sigma=30\%$ for method no. 1). Subsequent studies have shown, however, that silver particles prepared by either method serve well as cores for generating silver/gold core/shell nanoparticles.

B. Preparation of Silver/gold Core/shell Nanoparticles

This step describes gold shell growth on the surface of silver cores described above. For silver nanoparticles, gold shells were grown on the silver core surface by reduction of $HAuCl_4$ with the reducing agent $NaBH_4$. The reduced gold has affinity for the silver surface, in part, because of the low surface chemical potential of the silver nanoparticles and near-zero lattice mismatch between these two materials. Two methods for growing gold shells on silver core nanocrystals are described below and the resulting core/shell nanoparticles were compared, silver core particles were prepared by method no. 1 described above.

Method No. 1: Gold shells (approximately one-monolayer thick) were grown on the surface of the silver nanoparticles (0.25 nmol of silver particles in 100 ml of 0.3 mM sodium citrate aqueous solution) by simultaneous dropwise addition, at a rate of between about 50 μL~600 μL/min., of HAuCl$_4$ (2 mM) and NaBH$_4$ (6 mM) solutions (in Nanopure water) at 0° C. to the silver nanoparticle suspension. The simultaneous dropwise addition of dilute gold precursors inhibits the formation of gold cluster nucleation sites by keeping the concentration of these gold forming reagents at about 2 μM. After enough HAuCl$_4$ and NaBH$_4$ was added to the nanoparticles to produce one monolayer of gold on the particles (see Equation 1 for a calculation of shell thickness) addition was halted.

$$V_{core} = 4/3 * \pi * R^3;$$

$$V_{core/shell} = 4/3 * \pi * (R+a)^3, \quad \text{Equation 1:}$$

wherein a is the shell thickness, (0.3 nm for 1 monolayer of Au);

$$V_{shell} = V_{core/shell} - V_{core};$$

$$N_{shell} = d_{shell} * V_{shell} / FW_{shell};$$

wherein, $V_{shell}$ is volume of shell;
$N_{shell}$ is the amount in mole of the shell;
$d_{shell}$ is density of shell materials, (for gold, d=19.3 g/ml);
$FW_{shell}$, the formula weight of shell materials, (for gold, FW=196.97 amu)

Gold was added 5% excess, calculated assuming 12-nm spheres: 0.8 mg of HAuCl$_4$.3H$_2$O and 3.7 mg of NaBH$_4$. Once 5% excess was achieved, addition of the solutions was stopped (halting formation of the shell) and 30 μmol of Bis(p-sulfonatophenyl)phenylphosphine (BSPP) was added. The silver/gold core/shell nanoparticles were then purified by centrifugation and dispersed in Nanopure water (12.4 nm in diameter, (σ=18%)), giving a 96% yield and a ratio of silver to gold of about 5.5:1.

Method no. 2: Gold shells (approximately one-monolayer thick) were grown on the surface of the silver nanoparticles (0.25 nmol of silver particles in 100 ml of 0.3 mM sodium citrate aqueous solution) by simultaneously treating them with HAuCl$_4$ (2 mM) and NaBH$_4$ (6 mM) via dropwise addition at room temperature at a rate of between about 50 μL~600 μL/min. The simultaneous dropwise addition of dilute gold precursors inhibits the formation of gold cluster nucleation sites by keeping the concentration of these gold forming reagents at about 2 μM. After sufficient HAuCl$_4$ and NaBH$_4$ were added to the nanoparticles to produce one monolayer of gold on the particles (5% excess, calculated assuming 12-nm spheres: 0.8 mg of HAuCl$_4$.3H$_2$O and 3.7 mg of NaBH$_4$), the reaction was stopped and 30 μmol of BSPP was added. The silver/gold core/shell nanoparticles were then purified by centrifugation and dispersed in nanopure water, giving a weight percent yield of about 90%, and average particle size of about 12.5 nm, and an silver to gold ratio of about 6.3:1.

Comparison results: The core/shell nanoparticles produced via method no. 1 (synthesis at 0° C.) were found to have better stability in 0.5 M NaCl solution compared to core/shell nanoparticles produced by method no. 2 (synthesis at room temperature). This result may be due, in part, to a slower rate of shell growth at 0° C. than the growth rate at room temperature.

(c) Discussion

Figure 1B:
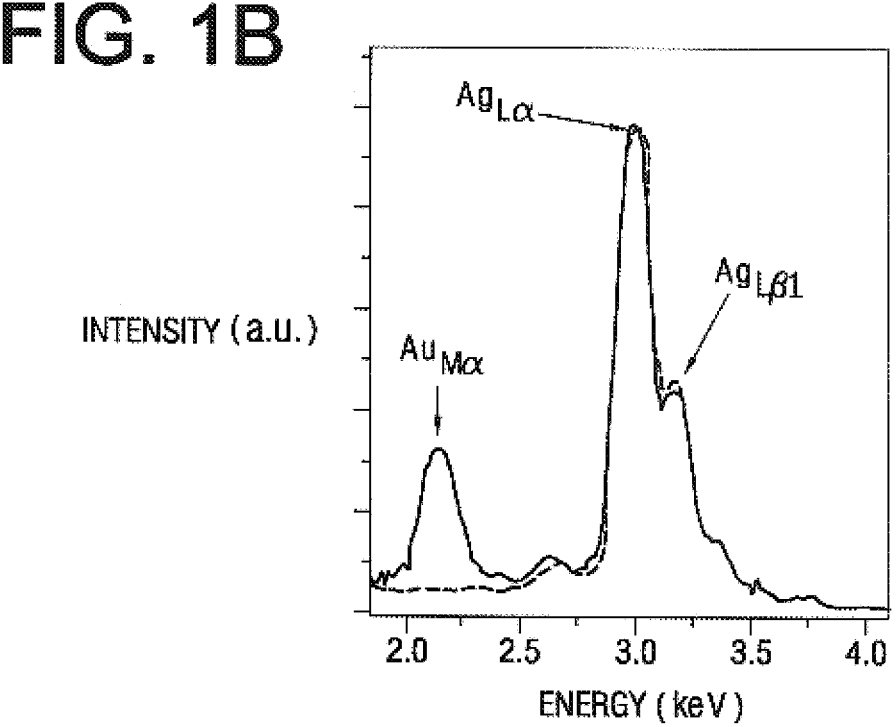

Silver nanoparticles were prepared by literature methods.[13] The particles were then passivated with BSPP (0.3 mM), purified by gradient centrifugation (collecting the primary fraction; ~12 nm in diameter), and dispersed in Nanopure water. Gold shells, approximately one-monolayer thick, were grown on the surface of the silver nanoparticles (0.25 nmol of silver particles in 100 mL of 0.3 mM sodium citrate aqueous solution) by simultaneously treating them with HAuCl$_4$ and sodium borohydride via dropwise addition at 0° C. The reduced gold has an affinity for the silver surface, in part, because of its near zero lattice mismatch.[14] The simultaneous dropwise addition of dilute gold precursors at 0° C. inhibits the formation of gold cluster nucleation sites by keeping the concentration of these gold forming reagents at about 2 μM. After enough HAuCl$_4$ and NaBH$_4$ were added to the nanoparticles to produce one monolayer of gold on the particles (5% excess, calculated assuming 12-nm spheres: 0.8 mg of HAuCl$_4$.3H$_2$O and 3.7 mg of NaBH$_4$), the reaction was stopped and 30 mM of BSPP (0.3 ml) was added. Then, the silver/gold core/shell nanoparticles were purified by centrifugation and dispersed in nanopure water (12.4 nm in diameter particles, (σ=18%). FIG. 1A shows a TEM image of silver/gold core/shell nanoparticles which was obtained using a Hitachi 8100 electron microscopy. A typical TEM sample was prepared by depositing one drop of nanoparticles solution onto a carbon coated copper grid. The excess solution was wicked away by filter paper and dry in vacuum. The silver:gold ratio in these core/shell particles was determined to be 5.2:1 by energy dispersive X-ray (EDX) microanalysis of the particles (FIG. 1B). FIG. 1B illustrates an EDX spectrum of silver core particles (dotted line) and silver/gold core/shell particles (solid line). L and M signify electron transitions into the L and M shell of the atoms, respectively, from higher states. EDX analysis was performed on a field emission scanning-electron microscopy (FESEM) Hitachi 4500. The SEM samples were prepared by depositing of one drop of nanoparticle solution on a silicon plate. The silver:gold ratio corresponds to an gold shell thickness of 3.1+/−0.6 Å, which correlates with approximately one monolayer of gold atoms.

Figure 1C:
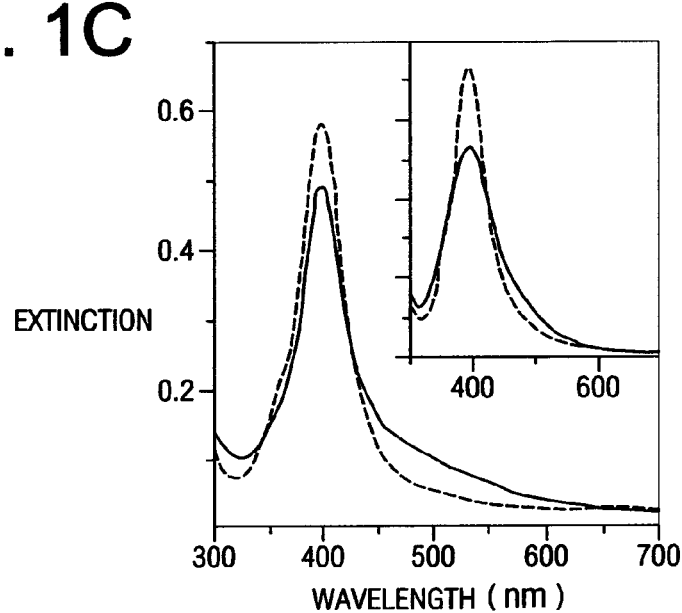

Significantly, the extinction spectrum of the core/shell particles is very similar to that for the citrate-stabilized pure silver particles. The surface plasmon band of the silver remains at the same wavelength but is dampened by about 10%, and the gold plasmon band is observed as a slight buckle at 500 nm. These spectral features provide strong evidence for gold shell growth. It should be noted that using different procedures, others have prepared gold-coated silver nanoparticles.[15] However, those procedures lead to silver/gold alloys;[15a] the extinction spectra of such particles exhibit characteristic red shifting and broadening of the plasmon resonance. Moreover, if one intentionally makes a solution of alloyed silver/gold particles, they can be easily distinguished from core/shell particles with comparable silver/gold ratios (see Supporting Information). Indeed, the core/shell silver/gold nanoparticles prepared by the methods of the instant invention retain the optical properties of the core with no observed red shifting of the silver plasmon band, (FIG. 1C). Using Mie theory, the extinction spectrum of a particle consisting of an 11.8 nm silver core and a monolayer gold shell was calculated.[11] The calculated spectrum was almost superimposable with the experimentally measured spectrum of the particles, (FIG. 1C, inset). FIG.

1C illustrates the UV-visible spectra of silver core (dotted line) and silver/gold core/shell (solid line) wherein the inset shows the calculated extinction spectra of silver particles (dotted line) and silver/gold core/shell particles (solid line). The UV/Vis spectra were obtained using a HP 8453 diode array spectrophotometer.

EXAMPLE 2

Preparation of Silver/gold Core/shell Nanoparticle-oligonucleotide Conjugates This Example describes the preparation of silver/gold core/shell nanoparticle oligonucleotide conjugates as probes for detecting a target nucleic acid. Two methods were employed and the resulting probes were then compared for stability. The oligonucleotide sequences used in making the conjugates are shown in FIG. 2a. These sequences were synthesized using standard phosphoramidite chemistry according to the literature. (James J. Storhoff, Robert Elghanian, Robert C. Mucic, Chad A. Mirkin, and Robert L. Letsinger, *J. Am. Chem. Soc.*, 1998, 120, 1959).

(a) Preparation of Core/shell Nanoparticle Conjugates

Method No. 1: Nanoparticle probes with appropriate probe oligonucleotides were prepared by derivatizing 10 mL of aqueous core/shell nanoparticle colloid (from method no. 1) with 8~10 OD (in about 500 uL) of alkanethiol-oligonucleotide (final oligonucleotide concentration is about 2 µM). After standing overnight (about 15 h), the solution was brought to 10 mM phosphate buffer (pH 7), using 100 mM concentrated phosphate buffer, and salt (from a 2 M aqueous NaCl solution) added to 0.05 M NaCl after 0.5 h, allowed to stand for about 8 h, then further addition of NaCl to 0.1 M, and after another standing time of about 8 h, another addition of NaCl to about 0.3 M and allowed to stand for a final ~8 h. To remove excess DNA, colloids were centrifuged for 30 min at 18,000 rpm using 1.5 mL eppendorf tubes. Following removal of the supernatant, the oily precipitate was washed with a volume equal to the discarded supernatant with 0.3 M NaCl, 10 mM phosphate buffer (pH 7) solution, centrifuged, and dispersed in 0.3 M NaCl, 10 mM phosphate buffer (pH 7), 0.01% azide solution. The final colloids were refrigerated and stored for later use.

Method No. 2: Nanoparticle probes with appropriate probe oligonucleotides were prepared by derivatizing 10 mL of aqueous colloid with 8~10 OD of alkanethiol-oligonucleotide (final oligonucleotide concentration is about 2 µM). After standing overnight (~15 h), the solution was brought to 10 mM phosphate buffer (pH 7), using 100 mM concentrated phosphate stock buffer, and salt added to 0.1 M NaCl, allowed to stand for about 20 h, and again, salt added to 0.3 M after another ~8 h. The mixture was allowed to stand for about 4 to 8 hours. To remove excess DNA, colloids were centrifuged for 30 min at 18,000 rpm using 1.5 mL eppendorf tubes. Following removal of the supernatant, the oily precipitate is washed with 0.3 M NaCl, 10 mM phosphate buffer (pH 7) solution in the same volume as the discarded supernatant, centrifuged, and dispersed in 0.3 M NaCl, 10 mM phosphate buffer (pH 7), 0.01% azide solution. The final colloids were refrigerated and stored for later use.

(b) Evaluation of Stability of Core/shell Nanoparticle Oligonucleotide Conjugates The core/shell nanoparticle oligonucleotide conjugates prepared by the two methods described above were compared using a salting procedure as described in each of the above 2 methods.

By method 1, the salt concentration was increased from 0.05 M NaCl to 0.1 M NaCl, and then to 0.3 M NaCl. By method 2, the salt concentration was increased in two steps: directly to 0.1 M NaCl and then to 0.3 M NaCl. Method 1 generates a higher quality nanoparticle-oligonucleotide conjugate when compared with those prepared by method 2. Via method 2, about 15% of the nanoparticle-oligonucleotide conjugates are not of adequate quality. Core/shell nanoparticle-oligonucleotide conjugate quality is evaluated by UV-Vis spectroscopy. Acceptable quality conjugates show a UV-Vis spectrum with the surface plasmon absorption peak centering at 400 nm, while poor (inadequate) quality conjugates show an absorption peak which is significantly damped and red-shifts to 450–550 nm.

(c) Discussion

The surface modification of these core/shell nanoparticles with 3'- and 5'-alkanethiol-capped oligonucleotides was accomplished using a procedure identical to the one used for 13-nm gold particles.[2d] Significantly, the oligonucleotide-modified particles exhibit the stability of the pure gold nanoparticles and can be suspended in 1M NaCl solution indefinitely. This represents a significant advantage over the oligonucleotide modified silver/gold alloy particles which irreversibly aggregate under comparable solution conditions and do not exhibit the stability of the oligonucleotide-modified core/shell particles of the instant invention.

Figure 1D:
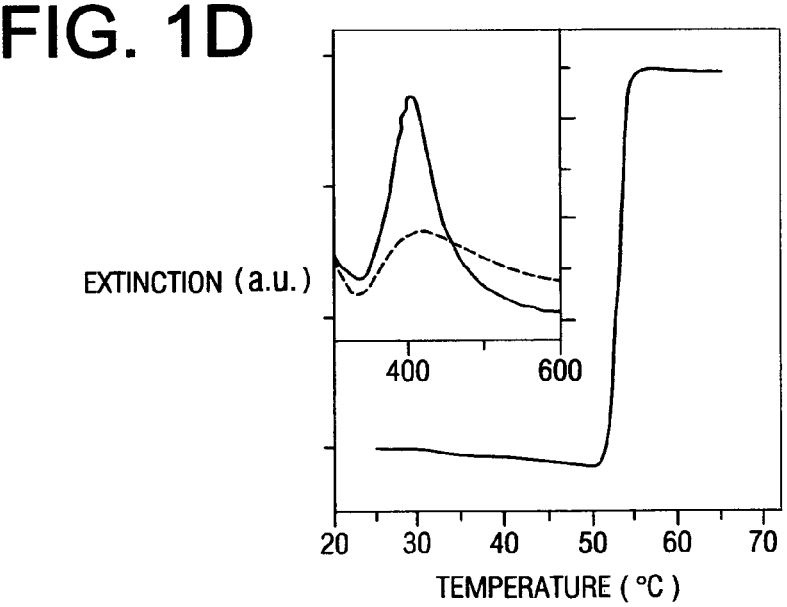
Figure 2:
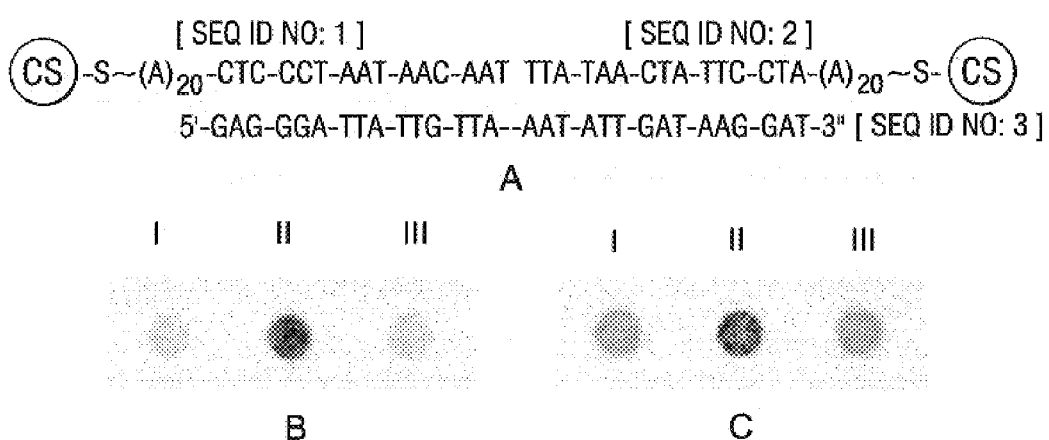
FIG. 2 illustrates (A) Mercaptoalkyl-oligonucleotide-modified Ag/gold core/shell particles and polynucleotide target. CS: core/shell; alkyl:propyl (left) and hexyl (right). DNA spot test using: (B) 12.4-nm Ag/gold nanoparticle probes and (C) 13-nm gold nanoparticle probes: (I) without target, (II) with target at room temperature, (III) with target at 58.0° C., a temperature above the $T_m$ (53.0° C.) of the hybridized DNA.

Moreover, the core/shell particles undergo hybridization with complementary linking oligonucleotides to form aggregated structures with a concomitant darkening of the solution; however, no distinct color change is observable by the naked eye (FIG. 2). Like the oligonucleotide modified pure gold nanoparticles, the nanoparticles comprising these silver/gold core/shell aggregate structures can be disassembled by heating the aggregates above the "melting temperature" ($T_m$) of the duplex linkers (FIG. 1D). UV-vis spectroscopy shows a red-shifting and dampening of the plasmon resonance of the core/shell particles upon DNA-induced assembly, (FIG. 1D, inset). FIG. 1D illustrates the thermal denaturation ("melting") curve of aggregates formed from hybridized oligonucleotide modified silver/gold core/shell particles in buffer solution (0.3 M NaCl and 10 mM phosphate buffer, pH=7). The oligonucleotide sequences are provided in FIG. 2A. The FIG. 1D inset shows the UV-visible spectra of dispersed oligonucleotide-modified silver/gold core/shell particles (solid line) and aggregated (dotted line) oligonucleotide-modified silver/gold core/shell particles formed via hybridization. UV-Vis spectra of silver and silver/gold core/shell particles (FIG. 1c and inset of FIG. 1d) was obtained is using a HP 8453 diode array spectrophotometer. The thermal denaturation experiment (FIG. 1D) was performed using an HP 8453 diode array spectrophotometer equipped with a HP 89090a Peltier temperature controller. The UV-Vis signature of the silver/gold core/shell probe/target oligonucleotide aggregates was recorded at 1 min intervals, as the temperature was increased from 25 to 70° C. with a holding time of 1 min/deg.

The particle assembly process induced by the complementary DNA also can be monitored on a $C_{18}$-reverse-phase alumina TLC plate, allowing for comparison with the pure gold system. The spot test results shown in FIGS. 2b and 2c were obtained as follows: a solution of the appropriate oligonucleotide target (24 pmol, 3 µL) was added to a 600 µL thin-wall PCR tube containing 200 µL of each silver/gold core/shell nanoparticle-oligonucleotide conjugates. After standing for 30 min at room temperature, the solution was transferred to a temperature controlled heater. After the set-point temperature was reached (monitored with an ethanol thermometer, 0.5° C. increments), the mixture was allowed to equilibrate for 5 min at which time 2.5 µL aliquots of the silver-gold probe/target oligonucleotide solution were transferred with a pipet onto the reverse-phase alumina plate and allowed to dry.

As shown in FIG. 2, with the core shell particles, a distinct yellow-to-dark brown color change is observed upon particle assembly in the presence of complementary target, FIGS. 2B-I and 2B-II. Note that when the solution temperature is above the $T_m$ of the DNA duplex linkers, a yellow spot is formed on the reverse phase alumina support, FIG. 2B-III. When one compares the properties of these new silver/gold core/shell probes with those derived from pure gold nanoparticles (with identical oligonucleotide sequences), FIG. 2C, one realizes that the core/shell particles provide a route to a second colorimetric change distinct from the gold system that ultimately could be used for monitoring two different oligonucleotide targets in one sample. Such capabilities could be important for both research-based and clinical genomic assays where multicolor formats are essential.[16]

EXAMPLE 3

Comparison of Silver, Silver/gold Core/shell and Silver/gold Alloy Nanoparticle Oligonucleotide Conjugates In this Example, the silver/gold core/shell nanoparticles prepared as described in Example 1 (method no. 1) were compared to gold nanoparticles[2] and silver/gold alloy nanoparticles prepared by literature methods. See Link, S.; Wang, Z. L.; El-Sayed, M. A. *J. Phys. Chem.B* 1999, 103, 3529. Following literature procedure, 0.8 mg of $HAuCl_4.3H_2O$ and 1.8 mg of $AgNO_3$ were dissolved in 95 ml of nanopure water. The solution was heated to reflux, and 5 ml of 1% sodium citrate was added to the solution. After refluxing an additional 30 min., the solution was allowed to cool to room temperature. The UV-Vis spectrum of the alloy particles exhibits a surface plasmon band at 428 nm with a full width at half-maximum (FWHM) of 90 nm (0.62 eV). In contrast, the UV-Vis spectrum of the silver/gold core/shell nanoparticle, with a comparable silver/gold ratio, exhibits a surface plasmon band at 400 nm with a FWHM of 58 nm (0.45 eV).

Figure 3:
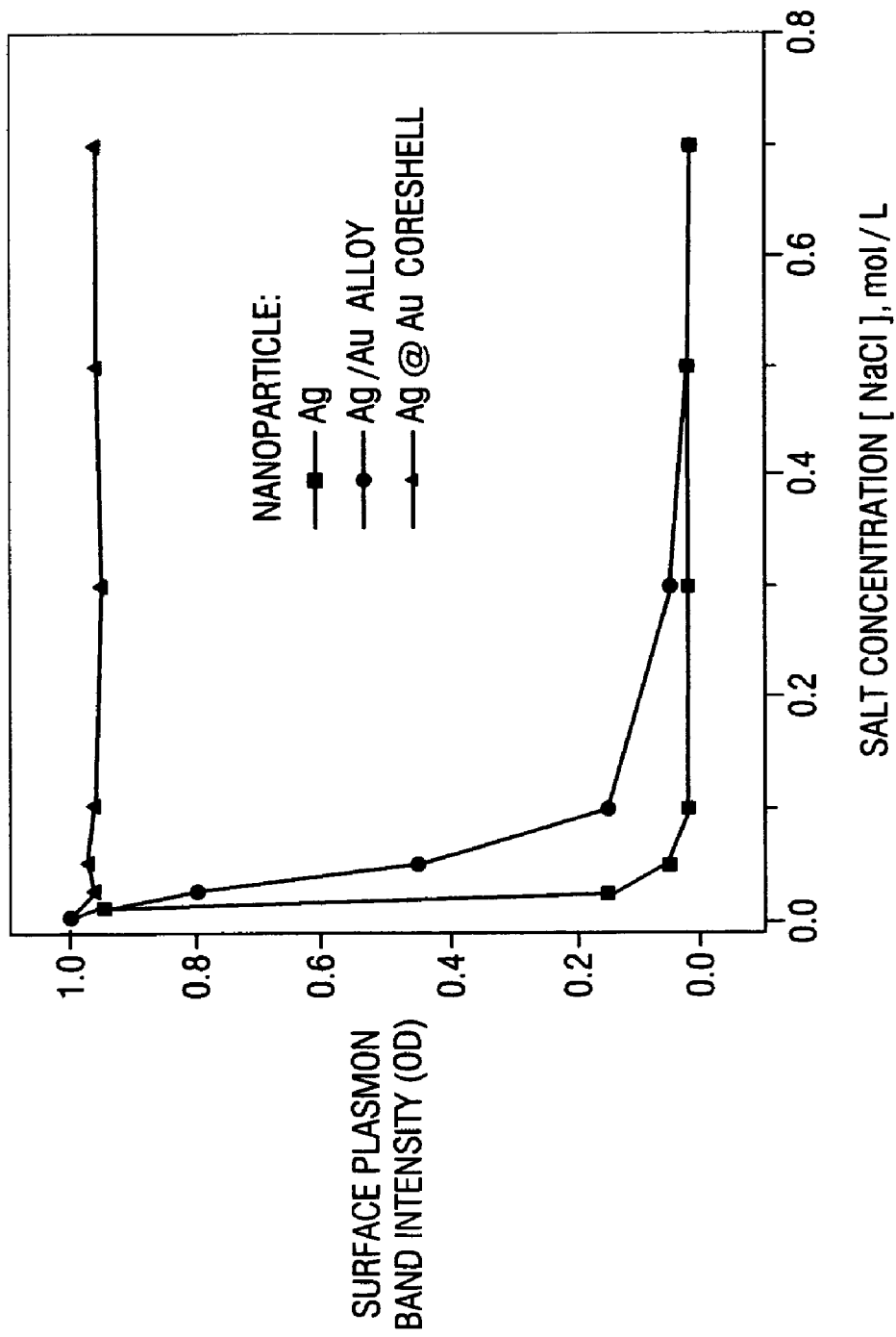
FIG. 3 illustrates the relative stabilities of Ag, Ag/Au alloy, and Ag/Au core/shell nanoparticle-oligonucleotide conjugates at different salt concentrations.

The surface modification of these core/shell and alloy nanoparticles with 3'- and 5'-alkanethiol-capped oligonucleotides was accomplished using a procedure identical to the one used for 13-nm gold particles. See Storhoff, J. J.; Elghanian, R.; Mucic, R. C.; Mirkin, C. A.; Letsinger, R. L. *J. Am. Chem. Soc.* 1998 120, 1959. Significantly, the oligonucleotide-modified core/shell nanoparticles exhibit the stability of the pure gold nanopaticles and can be suspended in 1M NaCl solutions indefinitely, FIG. 3. In contrast, the oligonucleotide-modified silver/gold alloy particles irreversibly aggregate when brought to a salt concentration of 0.1 M, FIG. 3.

Another way to evaluate stability of the particle/DNA conjugate uses a DNA melting test. The core/shell nanoparticle/DNA conjugate can reversibly hybridize with target DNA in a salt concentration range from 0.1 to 1.0 M, and the resulting nanoparticle aggregates can "melt" off when heated above the melting temperature. This hybridization/dehybridization process is completely reversible for core/shell particles. The core/shell particle/DNA conjugates show no degradation after 100 cycles, which contrasts sharply to silver/gold-alloy particle/DNA conjugates that irreversibly aggregate even under the low salt concentrations (0.05 M NaCl) necessary to effect DNA hybridization.

EXAMPLE 4

Preparation of Pt/gold Core/shell Nanoparticles

This Example describes the preparation of Pt/gold core/shell nanoparticles by the inventive process. In Part A, Pt core nanoparticles were prepared by hydrogen reduction of $K_2PtCl_4$ in an overnight reaction. In Part B, goldshells were grown on the Pt cores.

(a) Preparation of Pt Core Nanoparticles

In a 500-ml three-neck flask, $K_2PtCl_4$ (8.3 mg) and sodium polyacrylate (20 mg) were dissolved in 200 ml of Nanopure water. $H_2$ was bubbled into the reaction solution overnight with stirring. This resulted in Pt nanoparticles that were purified and isolated, yielding nanoparticles of about 12 nm in diameter.

Figure 4:
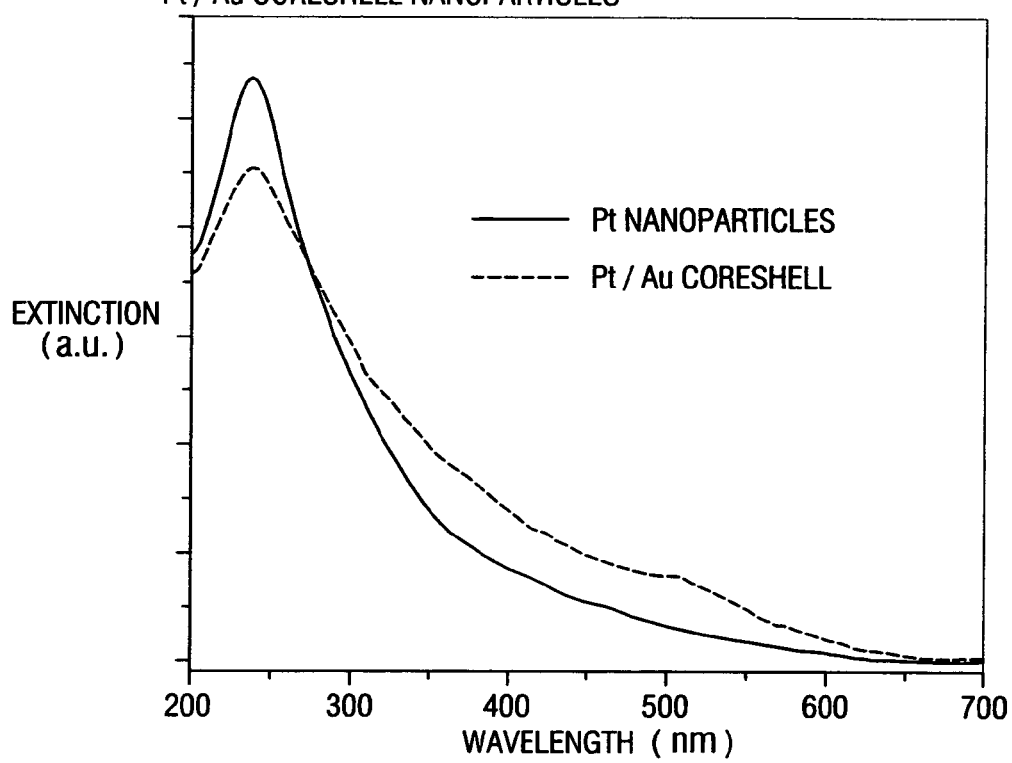
FIG. 4 illustrates the UV-VIS spectra of a Pt core (dotted line) and Pt/gold core/shell nanoparticles (solid line).

(b) Preparation of Pt/gold Core/shell Nanoparticles 100 ml of 12-nm Pt nanoparticle solution (0.25 nmol, as prepared according to the above procedure) was put into a 250-ml three-neck flask. To the nanoparticle solution were added $HAuCl_4$ and $NaBH_4$ dropwise, simultaneously, at 0° C. The simultaneous dropwise addition of dilute gold precursors inhibits the formation of gold cluster nucleation sites by keeping the concentration of these gold forming reagents at about 2 µM. After sufficient amounts of $HAuCl_4$ and $NaBH_4$ were added to the nanoparticles to produce one monolayer of gold on the Pt nanoparticles (5% excess, calculated assuming 12-nm spheres: 1.6 mg of $HAuCl_4.3H_2O$ and 4 mg of $NaBH_4$), addition of these reagents to the reaction was stopped. UV-Vis spectra of Pt core and Pt/gold core/shell nanoparticle are shown in FIG. 4.

EXAMPLE 5

Preparation of Magnetic $Fe_3O_4$/gold Core/shell Nanoparticles

Figure 6:
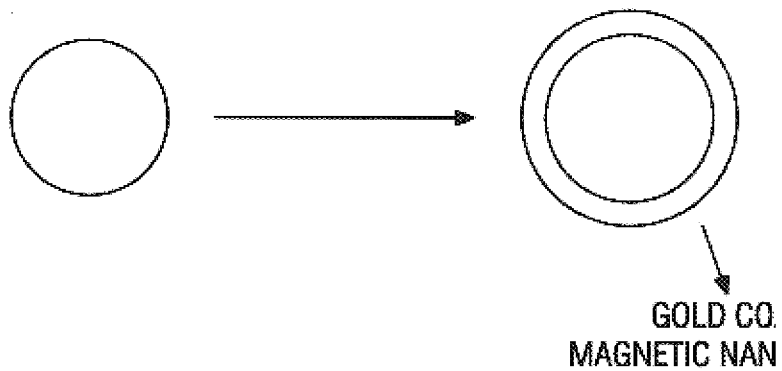
FIG. 6 illustrates the core/shell approach to magnetic gold nanoparticles. Some different classes of nanoparticle cores include (A) metal oxide magnetic cores; (B) pure metal cores; and (C) alloy metal cores.

This Example describes the preparation of magnetic gold nanoparticles by the inventive process. In Part A, $Fe_3O_4$ magnetic core nanoparticles were prepared. In Part B, goldshells were grown on the magnetic cores. Other magnetic cores could be used in place of $Fe_3O_4$ such as Co, Fe, Ni, FePt, and FeAu. FIG. 6 illustrates the core/shell approach to prepare magnetic gold nanoparticles.

(a) Preparation of $Fe_3O_4$ Core Nanoparticles

In a typical synthesis, $Fe_3O_4$ nanoparticles were prepared as follows. First, 0.86 g $FeCl_2.4H_2O$ and 2.35 g $FeCl_3.6H_2O$ were dissolved in 50 mL nanopure water under an inert $Ar_{(g)}$ atmosphere. The solution was heated to 80° C. with vigorous stirring. A solution of 100 mg of neat decanoic acid in 5 mL of acetone was added to the Fe solution, followed by 5 mL of 28% (w/w) $NH_3/H_2O$. Additional neat decanoic acid was added to the suspension in 5×0.2 g amounts over 5 min. The reaction was allowed to proceed for 30 min at 80° C. with stirring to produce a stable, water-based suspension. Following formation of the suspension, the reaction was cooled slowly to room temperature. The resulting $Fe_3O_4$ nanoparticles (5.0 nmol) were treated further with sodium thiorectic acid (0.1 mmol) solution overnight to allow for surface exchange at the particle surface. Sulfur ions replace oxygen on the surface of the $Fe_3O_4$ nanoparticles, providing the growth site for the goldshell. This ligand exchange process is also necessary for the preparation of $Co_3O_4$ magnetic cores.

(b) Preparation of Fe₃O₄/gold Core/shell Nanoparticles

Figure 5:
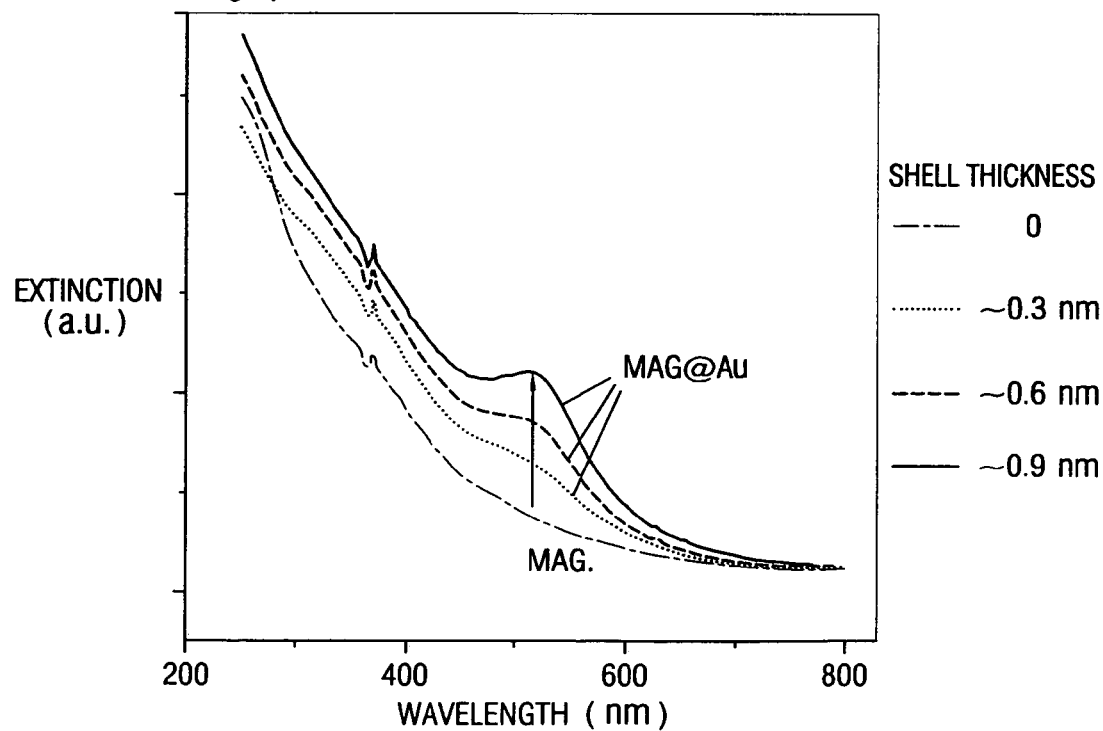
FIG. 5 illustrates the UV-VIS spectra of gold growth on the surface of $Fe_3O_4$ nanoparticles at 0, 0.3 nm, 0.6 nm, and 0.9 nm thickness.
Figure 7:
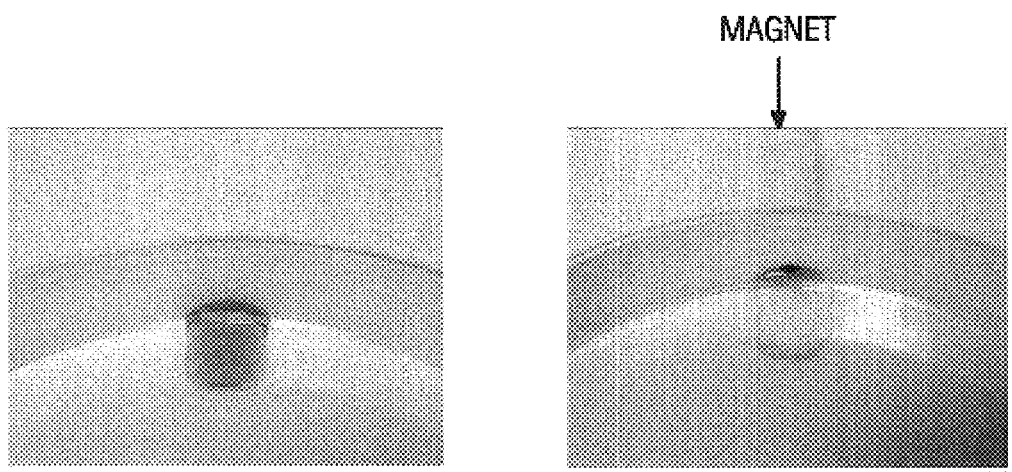
FIG. 7 illustrates the behavior of $Fe_3O_4$/gold core/shell particles as super paramagnetic particles in the presence of an applied magnetic field. In the presence of a magnetic field, a solution containing the magnetic gold nanoparticles appears red. When a magnetic force is applied over a period of 2 hours, the solution becomes colorless as the nanoparticles migrate towards the magnetic force.
Figure 8A:
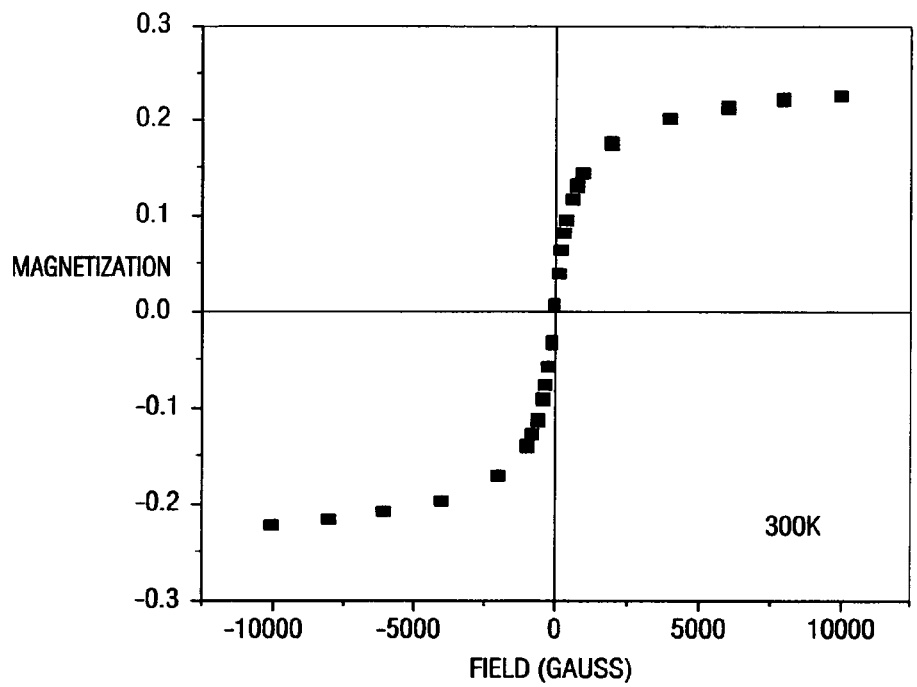
FIGS. 8(A) and (B) Magnetic properties of DNA functionalized magneto-gold nanoparticles; (C) TEM image of DNA functionalized magneto-gold nanoparticles (average diameter=18 nm, shell thickness=2 nm, (core diameter=14 nm)); (D) Melting curve for magneto-gold nanoparticle probes linked with target DNA, probe a=3'HS-$a_{20}$-ctc cct aat aac aat-5', probe b=3'tta taa cta ttc cta-$a_{20}$-SH5', target a'b'=5'-gag gga tta ttg tta . . . aat att gat aag gat-3'.
Figure 8B:
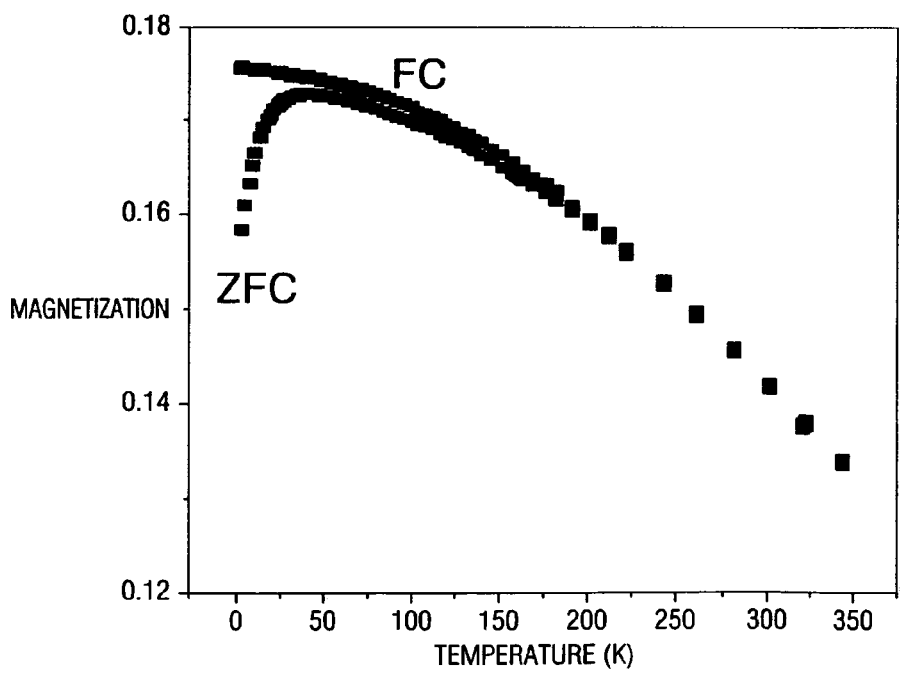
Figure 8C:
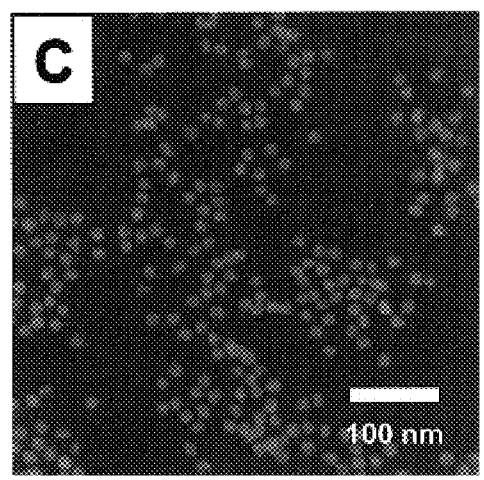
Figure 8D:
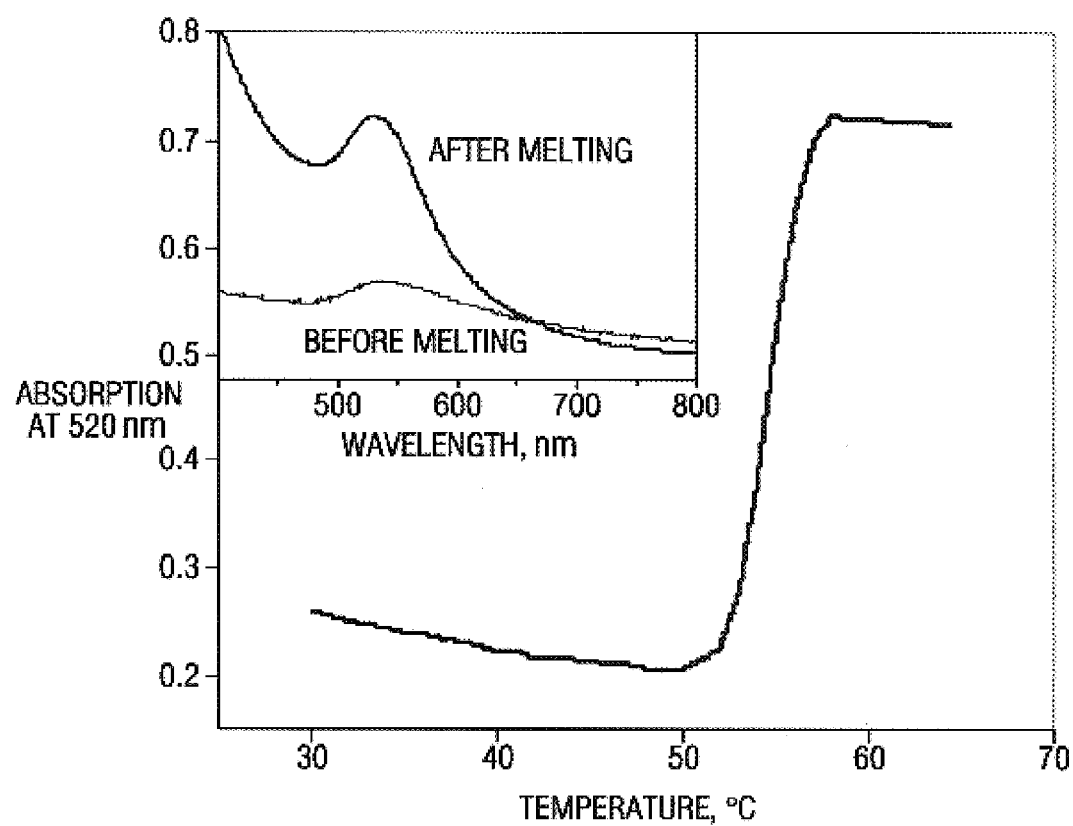

The procedure for growing gold shell is similar to that of core/shell silver/gold preparation described in Example 1. The UV-Vis spectrum, of the Fe₃O₄/gold shell growth is shown in FIG. 5. In an applied magnetic field, Fe₃O₄/gold core/shell particles behave as super paramagnetic particles (FIG. 7). Magnetic properties of DNA functionalized magneto-gold nanoparticles are shown in FIGS. 8(A) and (B). FIG. 8(C) shows a TEM image of DNA functionalized magneto-gold nanoparticles (average diameter=18 nm, shell thickness=2 nm, (core diameter=14 nm)) and (D) shows a Melting curve for magneto-gold nanoparticle probes linked with target DNA, probe a=3'HS-a₂₀-ctc cct aat aac aat-5', probe b=3'tta taa cta ttc cta-a₂₀-SH5', target a'b'=5'-gag gga tta ttg tta . . . aat att gat aag gat-3'.

EXAMPLE 6

Preparation of Magnetic Co/gold Core/shell Nanoparticles

This Example describes the preparation of magnetic gold nanoparticles by the inventive process. In Part A, Co magnetic core nanoparticles were prepared. In Part B, gold shells were grown on the Co magnetic cores.

(a) Preparation of Co Nanoparticle Cores

Figure 9:
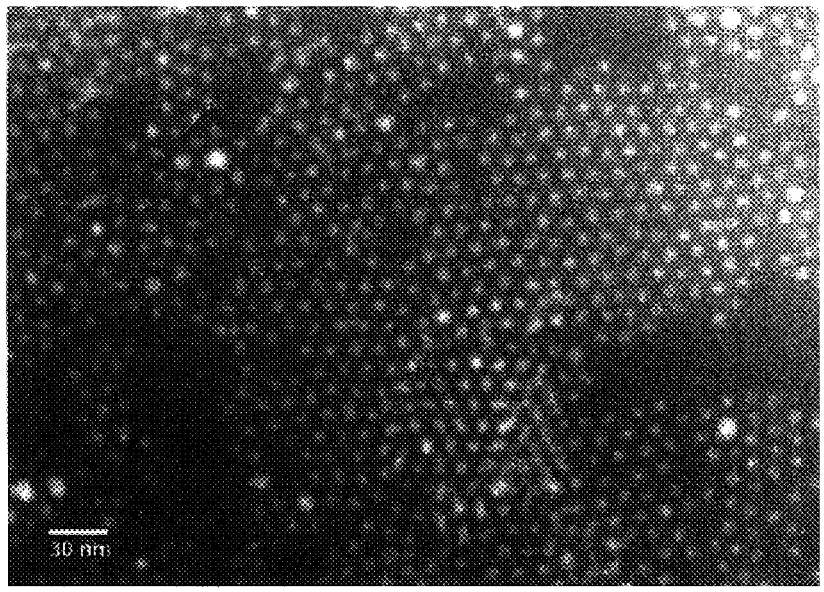
FIG. 9 illustrates the TEM image of Co nanoparticles.

O-dichlorobenzene (15.9 g), trioctylphosphine oxide (0.1 g), and 0.2 ml of oleic acid were placed into a 50-ml tri-neck flask, and heated to 180° C. A solution of Co₂(CO)₈ (0.65 g in 3 ml of O-dichlorobenzene) was added by injection into the heated solution. After this addition, the reaction temperature was maintained at 180° C. for an hour. The reaction solution was then cooled to room temperature. Co nanoparticles of about 12 nm in diameter were produced in a yield of 95%. FIG. 9 shows the TEM image for the Co nanoparticles.

(b) Preparation of Co/gold Core/shell Nanoparticles

The following is a typical coating protocol for Co/gold core/shell nanoparticles.

After Co nanoparticles (0.01 μmol) were dissolved in O-dichlorobenzene (12 g) in a 50-ml tri-neck flask, trioctylphosphine oxide (0.1 g) was added in the Co solution. The solution was heated to 180° C., at which point the gold-shell stock solutions 1 and 2 (see below) were added dropwise, simultaneously, to the hot reaction solution, at a rate of about 50 μl–500 μl/min. After sufficient amount of stock solutions 1 and 2 were added (about 5% excess), the reaction solution was maintained at 180° C. for another 30 mins. Subsequently, the reaction was cooled to room temperature in order to halt it.

The gold shell stock solutions were prepared as follows: stock solution 1, HAuCl₄.3H₂O (0.1 g) and n-hexadecyltrimetyl ammonium bromide (0.1 g) were dissolved in O-dichlorobenzene (10 g); stock solution 2, 1,1-hexadecanediol (0.12 g) was dissolved in O-dichlorobenzene (10 g).

EXAMPLE 7

Preparation of CdS, CdSe,/gold Core/shell Nanoparticles

This Example describes the preparation of gold-coated semiconductor quantum dots by the inventive process. In Part A, CdSe (or CdS) semiconductor core nanoparticles were prepared. In Part B, gold shells were grown on the CdS, CdSe semiconductor cores.

(a) Preparation of CdSe (or CdS) Nanoparticle Cores

Nanopure water (100 ml), sodium citrate (100 mg), and cadmium perchlorate (25 mg) were placed into a 250-ml tri-neck flask, and the pH of the solution was adjusted to about 9.0. Bubbling with Ar for 30 min, then the solution was heated to 100° C. A solution (4 ml, 0.02M) of 1,3-dimethyl-2-selenourea (or 1,3-dimethyl-2-thiourea) was injected into the hot solution. After 2 min, the solution was cooled to room temperature. The CdSe (or CdS) nanoparticles was separated from the solution by Centricon filtration, and redispersed in nanopure water.

(b) Preparation of CdSe (or CdS)/gold Core/shell Nanoparticles

The following is a typical coating protocol for CdSe (or CdS)/gold core/shell nanoparticles.

After CdSe (or CdS) nanoparticles (~4 nm in diameter, 10 nmol) were dissolved in nanopure water (100 ml) in a 250-ml tri-neck flask, sodium citrate (0.2 g) was added in the nanoparticle solution. The solution was cooled to 0° C., at which point the gold-shell stock solutions 1 and 2 (see below) were simultaneously added, dropwise, to the reaction solution, at a rate of about 50 μl–200 μl/min. After sufficient amount of stock solutions 1 and 2 were added (about 5% excess), the reaction solution was maintained at 0° C. for another 30 min. Subsequently, the reaction solution was warmed to room temperature. Separated from the solution by Centricon filtration, CdSe (or CdS)/gold core/shell nanoparticles were obtained.

The gold shell stock solutions were prepared as follows: stock solution 1, HAuCl₄.3H₂O (4.1 mg) was dissolved in nanopure water (5 ml); stock solution 2, NaBH₄ (7.4 mg) was dissolved in nanopure water at 0° C. (5 ml), and keep in 0° C. for use.

REFERENCES

1. Mirkin, C. A.; Letsinger, R. L., Mucic, R. C.; Storhoff, J. J. *Nature* 1996, 382, 607.
2. (a) Elghanian, R.; Stohoff, J. J.; Mucic, R. C.; Letsinger, R. L.; Mirkin, C. A. *Science* 1997, 277, 1078. (b) Taton, T. A.; Letsinger, R. L.; Mirkin, C. A. *Science* 1999, 289, 1757. (c) Taton, T. A.; Lu, G.; Mirkin, C. A. *J. Am. Chem. Soc.* 2001, 123, 5164. (d) Storhoff, J. J.; Elghanian, R.; Mucic, R. C.; Mirkin, C. A.; Letsinger, R. L. *J. Am. Chem. Soc.* 1998 120, 1959.
3. (a) Mann, S.; Shenton, W.; Li, M.; Connolly, S. Fitzmaurice, D. *Adv. Mater.* 2000, 12, 147. (b) Niemeyer, C. M.; Burger, W.; Peplies, J. *Angew. Chem., Int. Ed.* 2000, 37, 2265.
4. Alivisatos, A. P.; Johnsson, K. P.; Peng, X.; Wilson, T. E.; Loweth C. J.; Bruchez, M. P., Jr.; Schultz, P. G. *Nature* 1996, 382, 609.
5. Mitchell, G. P.; Mirkin, C. A.; Letsinger R. L. *J. Am. Chem. Soc.* 1999, 121, 8122.
6. Chan, W. C. W.; Nie, S. *Science* 1998, 281, 2016.
7. Mattoussi, H.; Mauro, J. M.; Goldman, E. R.; Anderson, G. P. Sundar V. C.; Mikulec F. V., Bawendi, M. G. *J. Am. Chem. Soc.* 2000, 122, 12142.
8. He, L.; Musick, D. M.; Nicewarner, S. R.; Ssalinas, F. G.; Benkovic, S. J. Natan, M. J.; Keating, C. D. *J. Am. Chem. Soc.* 2000, 122, 9071.
9. Pathak, S.; Choi, S. K.; Arnheim, N.; Thompson, M. E. *J. Am. Chem. Soc.* 2001, 123, 4103.
10. Martin, B. R.; Dermody, D. J.; Reiss, B. D.; Fang, M.; Lyon, L. A.; Natan, M. J.; Mallouk, T. E. *Adv. Mater.* 1999, 11,1021.
11. Mulvaney, P. *Langmuir* 1996, 12, 788.

12. Link, S.; Wang, Z. L.; El-Sayed, M. A. *J. Phys. Chem.B* 1999, 103, 3529.
13. Ung, T.; Liz-Marzan, L. M.; Mulvaney, P. *Langmuir* 1998, 14, 3740.
14. Lide, D. R. Eds, *Handbook of Chemistry and Physics*, CRC press: Boca Raton, 1992.
15. (a) Mulvaney, P.; Giersig, M.; Henglein, A. *J. Phys. Chem.* 1993, 97, 7061. (b) Rivas, L.; Sanchez-Cortes, S.; Garcia-Ramos; J. V.; Morcillo, G. *Langmuir* 2000, 16, 9722. (c) Ygeurabide U.S. Pat. No. 6,214,560.
16. Schrock. E.; duManoir, S.; Veldman, T.; Schoell. B.; Wienberg, J.; FergusonSmith, M. A.; Ning, Y.; Ledbetter, D. H.; BarAm, I.; Soenksen, D.; Garini, Y.; Ried, T. *Science*, 1996, 273, 494.

We claim:

1. A method for preparing core/shell nanoparticles comprising the steps of:
   (a) providing metal-containing cores;
   (b) treating the metal-containing cores simultaneously with a solution comprising a gold salt and a solution comprising a reducing agent so as to form a reaction mixture having a gold salt concentration of about 2 uM and generate a non-alloying gold shell surrounding the nanoparticle cores to produce core/shell nanoparticles; and
   (c) isolating the core/shell nanoparticles.

2. The method according to claim 1 wherein the gold salt comprises $HAuCl_4$, $NaAuCl_4$, $KAuCl_4$, or $KAu(CN)_2$.

3. The method according to claim 1 wherein the gold salt comprises $HAnCl_4$.

4. The method according to claim 1 wherein the reducing agent comprises $NaBH_4$, ascorbic acid, $NH_2OH$, or $N_2H_4$.

5. The method according to claim 4 wherein the reducing agent comprises $NaBH_4$.

6. The method according to claim 1, wherein the gold salt and reducing agent are present at a ratio ranging from about 1:2 uM:uM to about 1:20 uM:uM.

7. The method according to claim 1, wherein the metal-containing core comprises silver, Pt, FePt, FeAu, AgAu, Fe, Co, or Ni.

8. The method according to claim 1, wherein the core comprises silver.

9. The method according to claim 1, wherein the metallic nanoparticle core comprises an alloy metal comprising FePt or FeAu.

10. The method according to claim 1, wherein the metal-containing core comprises a metal oxide.

11. The method according to claim 1, wherein the metal-containing core is magnetic.

12. The method according to claim 11, wherein the metal-containing core comprises $Fe_3O_4$ or $Co_3O_4$.

13. The method according to claim 1, wherein the metal-containing core comprises a semiconductor.

14. The method according to claim 13, wherein the metal-containing core comprises CdSe or CdS.

* * * * *

UNITED STATES PATENT AND TRADEMARK OFFICE
CERTIFICATE OF CORRECTION

| | | |
|---|---|---|
| PATENT NO. | : 7,147,687 B2 | Page 1 of 1 |
| APPLICATION NO. | : 10/153483 | |
| DATED | : December 12, 2006 | |
| INVENTOR(S) | : Chad A. Mirkin, Yun-Wei Cao and Rongchao Jin | |

It is certified that error appears in the above-identified patent and that said Letters Patent is hereby corrected as shown below:

Title Page;

In the Face of the Patent, in numerical identifier (73), please replace "Nanosphere, Inc., Northbrook, IL (US)" with --Northwestern University, Evanston, IL (US)--

Signed and Sealed this

Seventeenth Day of June, 2008

JON W. DUDAS
*Director of the United States Patent and Trademark Office*